(12) United States Patent
Djupesland

(10) Patent No.: US 10,737,045 B2
(45) Date of Patent: Aug. 11, 2020

(54) DELIVERY DEVICES

(71) Applicant: OptiNose AS, Oslo (NO)

(72) Inventor: Per Gisle Djupesland, Oslo (NO)

(73) Assignee: OptiNose AS, Oslo (NO)

( * ) Notice: Subject to any disclaimer, the term of this patent is extended or adjusted under 35 U.S.C. 154(b) by 1183 days.

(21) Appl. No.: 14/864,365

(22) Filed: Sep. 24, 2015

(65) Prior Publication Data

US 2016/0263334 A1  Sep. 15, 2016

Related U.S. Application Data

(63) Continuation of application No. 14/456,767, filed on Aug. 11, 2014, now Pat. No. 9,168,341, which is a (Continued)

(30) Foreign Application Priority Data

Aug. 28, 2003 (GB) .................................. 0320171.2

(51) Int. Cl.
*A61M 15/00* (2006.01)
*A61M 15/08* (2006.01)
*A61M 11/00* (2006.01)

(52) U.S. Cl.
CPC ...... *A61M 15/0098* (2014.02); *A61M 11/001* (2014.02); *A61M 15/00* (2013.01); *A61M 15/002* (2014.02); *A61M 15/0013* (2014.02); *A61M 15/0021* (2014.02); *A61M 15/0028* (2013.01); *A61M 15/0031* (2014.02); *A61M 15/08* (2013.01); *A61M 15/0083* (2014.02); *A61M 2202/30* (2013.01); *A61M 2205/7518* (2013.01)

(58) Field of Classification Search
None
See application file for complete search history.

(56) References Cited

U.S. PATENT DOCUMENTS 605,436 A   6/1898  Kellogg
642,748 A   2/1900  Manners
(Continued)

FOREIGN PATENT DOCUMENTS

EP   1 220 700 B1   4/2003
GB   501564         3/1939
(Continued)

OTHER PUBLICATIONS

English-Language Abstract of WO 01/24857 A1.
(Continued)

*Primary Examiner* — Rachel T Sippel
(74) *Attorney, Agent, or Firm* — Finnegan, Henderson, Farabow, Garrett & Dunner, LLP

(57) ABSTRACT

A delivery device for and method of delivering substance, the delivery device comprising: an outlet member through which substance is in use delivered in an entraining gas flow; and a substance supply unit for supplying substance to be entrained by an entraining gas flow as one or both of a vapor or a fine aerosol mist, wherein the substance supply unit comprises a flow channel which is fluidly connected to the outlet member, and a substance supporting element for supporting substance, at least a surface of which is in use disposed in the flow channel.

5 Claims, 16 Drawing Sheets

Related U.S. Application Data continuation of application No. 10/570,034, filed as application No. PCT/IB2004/003004 on Aug. 29, 2004, now Pat. No. 8,800,555.

(56) References Cited

U.S. PATENT DOCUMENTS

| | | |
|---|---|---|
| 658,436 A | 9/1900 | Groth |
| 746,749 A | 12/1903 | Seidel |
| 794,641 A | 7/1905 | Ramey |
| 902,832 A | 11/1908 | Philbrook |
| 3,722,509 A | 3/1973 | Nebel |
| 3,971,377 A | 7/1976 | Damani |
| 4,273,124 A * | 6/1981 | Zimmerman ..... A61M 16/0666 128/207.18 |
| 4,275,722 A | 6/1981 | Sorensen |
| 4,765,348 A | 8/1988 | Honeycutt |
| 4,800,903 A | 1/1989 | Ray et al. |
| 4,813,437 A | 3/1989 | Ray |
| 5,101,838 A | 4/1992 | Schwartz et al. |
| 5,161,524 A | 11/1992 | Evans |
| 5,373,841 A | 12/1994 | Kyllonen et al. |
| 5,435,301 A | 7/1995 | Herold et al. |
| 5,692,496 A | 12/1997 | Casper et al. |
| 5,782,232 A | 7/1998 | Rowland |
| 5,797,392 A | 8/1998 | Keldmann et al. |
| 5,881,719 A | 3/1999 | Gottenauer et al. |
| 6,039,042 A | 3/2000 | Sladek |
| 6,085,742 A | 7/2000 | Wachter et al. |
| 6,092,522 A | 7/2000 | Calvert et al. |
| 6,102,036 A * | 8/2000 | Slutsky ............ A61M 15/0045 128/202.21 |
| 6,591,832 B1 | 7/2003 | DeJonge |
| 6,595,209 B1 | 7/2003 | Rose et al. |
| 6,648,848 B1 | 11/2003 | Keldmann et al. |
| 6,698,425 B1 | 3/2004 | Widerström |
| 6,715,485 B1 | 4/2004 | Djupesland |
| 6,729,328 B2 | 5/2004 | Goldemann |
| 6,811,543 B2 | 11/2004 | Keldmann et al. |
| 7,073,499 B1 | 7/2006 | Reinhold et al. |
| D530,815 S | 10/2006 | Murphy et al. |
| 7,163,013 B2 | 1/2007 | Harrison |
| 7,347,201 B2 | 3/2008 | Djupesland |
| 7,353,823 B2 | 4/2008 | Tsutsui |
| 7,377,901 B2 | 5/2008 | Djupesland et al. |
| 7,481,218 B2 | 1/2009 | Djupesland |
| 7,543,581 B2 | 6/2009 | Djupesland |
| 7,740,014 B2 | 6/2010 | Djupesland |
| 7,784,460 B2 | 8/2010 | Djupesland et al. |
| 7,841,337 B2 | 11/2010 | Djupesland |
| 7,854,227 B2 | 12/2010 | Djupesland |
| 7,934,503 B2 | 5/2011 | Djupesland et al. |
| 7,975,690 B2 | 7/2011 | Djupesland |
| 8,047,202 B2 | 11/2011 | Djupesland |
| 8,146,589 B2 | 4/2012 | Djupesland |
| 8,171,929 B2 | 5/2012 | Djupesland et al. |
| 8,327,844 B2 | 12/2012 | Djupesland |
| 8,511,303 B2 | 8/2013 | Djupesland |
| 8,522,778 B2 | 9/2013 | Djupesland |
| 8,550,073 B2 | 10/2013 | Djupesland |
| 8,555,877 B2 | 10/2013 | Djupesland |
| 8,555,878 B2 | 10/2013 | Djupesland |
| 8,590,530 B2 | 11/2013 | Djupesland et al. |
| 8,596,278 B2 | 12/2013 | Djupesland |
| 8,800,555 B2 | 8/2014 | Djupesland |
| 8,875,704 B2 | 11/2014 | Djupesland et al. |
| 8,899,229 B2 | 12/2014 | Djupesland et al. |
| 8,910,629 B2 | 12/2014 | Djupesland et al. |
| D723,156 S | 2/2015 | Djupesland et al. |
| D725,769 S | 3/2015 | Djupesland et al. |
| 8,978,647 B2 | 3/2015 | Djupesland et al. |
| 9,010,325 B2 | 4/2015 | Djupesland et al. |
| 9,038,630 B2 | 5/2015 | Djupesland et al. |
| 9,067,034 B2 | 6/2015 | Djupesland et al. |
| 9,072,857 B2 | 7/2015 | Djupesland |
| 9,108,015 B2 | 8/2015 | Djupesland |
| 9,119,932 B2 | 9/2015 | Djupesland |
| 9,132,249 B2 | 9/2015 | Djupesland |
| 9,144,652 B2 | 9/2015 | Djupesland et al. |
| 9,168,341 B2 | 10/2015 | Djupesland |
| 9,205,208 B2 | 12/2015 | Djupesland |
| 9,205,209 B2 | 12/2015 | Djupesland |
| 9,272,104 B2 | 3/2016 | Djupesland |
| D759,805 S | 6/2016 | Djupesland |
| D761,951 S | 7/2016 | Djupesland |
| 9,452,272 B2 | 9/2016 | Djupesland et al. |
| 9,468,727 B2 | 10/2016 | Djupesland |
| D773,644 S | 12/2016 | Djupesland |
| 9,522,243 B2 | 12/2016 | Djupesland |
| 9,566,402 B2 | 2/2017 | Djupesland |
| 9,649,456 B2 | 5/2017 | Djupesland et al. |
| D809,128 S | 1/2018 | Djupesland |
| 2002/0157677 A1 | 10/2002 | Gonda et al. |
| 2002/0165482 A1 | 11/2002 | Keldmann et al. |
| 2003/0000523 A1 | 1/2003 | Citterio |
| 2003/0164169 A1 | 9/2003 | Stangl et al. |
| 2003/0172930 A1 | 9/2003 | Kullik et al. |
| 2004/0011356 A1 | 1/2004 | Sullivan |
| 2004/0024330 A1 | 2/2004 | Djupesland et al. |
| 2004/0031486 A1 | 2/2004 | Schwarze et al. |
| 2004/0094146 A1 | 5/2004 | Schiewe et al. |
| 2004/0112378 A1 | 6/2004 | Djupesland |
| 2004/0112379 A1 | 6/2004 | Djupesland |
| 2004/0112380 A1 | 6/2004 | Djupesland |
| 2004/0123864 A1 | 7/2004 | Hickey et al. |
| 2004/0149289 A1 | 8/2004 | Djupesland |
| 2004/0182388 A1 | 9/2004 | Djupesland |
| 2005/0028812 A1 | 2/2005 | Djupesland |
| 2005/0028813 A1 | 2/2005 | Harrison |
| 2005/0072430 A1 | 4/2005 | Djupesland |
| 2005/0235992 A1 | 10/2005 | Djupesland |
| 2006/0096589 A1 | 5/2006 | Djupesland |
| 2006/0107957 A1 | 5/2006 | Djupesland |
| 2006/0169278 A1 | 8/2006 | Djupesland et al. |
| 2006/0219240 A1 | 10/2006 | Djupesland |
| 2006/0219241 A1 | 10/2006 | Djupesland |
| 2006/0225732 A1 | 10/2006 | Djupesland |
| 2006/0231094 A1 | 10/2006 | Djupesland |
| 2007/0039614 A1 | 2/2007 | Djupesland |
| 2007/0125371 A1 | 6/2007 | Djupesland |
| 2007/0186927 A1 | 8/2007 | Djupesland et al. |
| 2008/0161771 A1 | 7/2008 | Djupesland |
| 2008/0163874 A1 | 7/2008 | Djupesland |
| 2008/0221471 A1 | 9/2008 | Djupesland et al. |
| 2008/0223363 A1 | 9/2008 | Djupesland |
| 2008/0289629 A1 | 11/2008 | Djupesland et al. |
| 2009/0101146 A1 | 4/2009 | Djupesland |
| 2009/0293873 A1 | 12/2009 | Djupesland et al. |
| 2009/0304802 A1 | 12/2009 | Djupesland et al. |
| 2009/0314293 A1 | 12/2009 | Djupesland |
| 2009/0320832 A1 | 12/2009 | Djupesland |
| 2010/0035805 A1 | 2/2010 | Hafner |
| 2010/0051022 A1 | 3/2010 | Djupesland et al. |
| 2010/0057047 A1 | 3/2010 | Djupesland et al. |
| 2010/0199984 A1 | 8/2010 | Williams et al. |
| 2010/0242959 A1 | 9/2010 | Djupesland et al. |
| 2010/0282246 A1 | 11/2010 | Djupesland et al. |
| 2010/0288275 A1 | 11/2010 | Djupesland et al. |
| 2010/0300439 A1 | 12/2010 | Djupesland et al. |
| 2011/0023869 A1 | 2/2011 | Djupesland |
| 2011/0053827 A1 | 3/2011 | Hafner |
| 2011/0088690 A1 | 4/2011 | Djupesland et al. |
| 2011/0088691 A1 | 4/2011 | Djupesland |
| 2011/0114087 A1 | 5/2011 | Djupesland et al. |
| 2011/0120456 A1 | 5/2011 | Immel |
| 2011/0126830 A1 | 6/2011 | Djupesland et al. |
| 2011/0259329 A1 | 10/2011 | Djupesland et al. |
| 2011/0318345 A1 | 12/2011 | Djupesland |
| 2012/0000459 A1 | 1/2012 | Djupesland |
| 2012/0006323 A1 | 1/2012 | Djupesland |
| 2012/0073571 A1 | 3/2012 | Djupesland |
| 2012/0090608 A1 | 4/2012 | Djupesland et al. |
| 2012/0260915 A1 | 10/2012 | Djupesland |
| 2013/0098362 A1 | 4/2013 | Djupesland et al. |

(56) References Cited

U.S. PATENT DOCUMENTS

| | | |
|---|---|---|
| 2013/0125889 A1 | 5/2013 | Djupesland et al. |
| 2013/0327320 A1 | 12/2013 | Djupesland |
| 2014/0018295 A1 | 1/2014 | Djupesland |
| 2014/0041660 A1 | 2/2014 | Djupesland et al. |
| 2014/0060536 A1 | 3/2014 | Djupesland |
| 2014/0073562 A1 | 3/2014 | Djupesland |
| 2014/0144442 A1 | 5/2014 | Djupesland et al. |
| 2014/0144443 A1 | 5/2014 | Djupesland et al. |
| 2014/0166008 A1 | 6/2014 | Djupesland |
| 2014/0202456 A1 | 7/2014 | Djupesland |
| 2014/0246022 A1 | 9/2014 | Djupesland et al. |
| 2015/0007811 A1 | 1/2015 | Djupesland et al. |
| 2015/0013670 A1 | 1/2015 | Djupesland et al. |
| 2015/0013677 A1 | 1/2015 | Djupesland et al. |
| 2015/0053201 A1 | 2/2015 | Djupesland et al. |
| 2015/0090259 A1 | 4/2015 | Djupesland et al. |
| 2015/0101605 A1 | 4/2015 | Djupesland et al. |
| 2015/0144129 A1 | 5/2015 | Djupesland et al. |
| 2015/0165139 A1 | 6/2015 | Hafner |
| 2015/0182709 A1 | 7/2015 | Djupesland |
| 2015/0246194 A1 | 9/2015 | Djupesland et al. |
| 2015/0367090 A1 | 12/2015 | Djupesland et al. |
| 2015/0367091 A1 | 12/2015 | Djupesland et al. |
| 2016/0001022 A1 | 1/2016 | Djupesland et al. |
| 2016/0045687 A1 | 2/2016 | Djupesland |
| 2016/0051778 A1 | 2/2016 | Djupesland et al. |
| 2016/0074603 A1 | 3/2016 | Djupesland et al. |
| 2016/0082206 A1 | 3/2016 | Djupesland et al. |
| 2016/0082207 A1 | 3/2016 | Djupesland et al. |
| 2016/0095989 A1 | 4/2016 | Djupesland |
| 2016/0095993 A1 | 4/2016 | Djupesland |
| 2016/0101249 A1 | 4/2016 | Djupesland |
| 2016/0166788 A1 | 6/2016 | Djupesland et al. |
| 2016/0184537 A1 | 6/2016 | Djupesland |
| 2016/0193435 A1 | 7/2016 | Djupesland |
| 2016/0250408 A1 | 9/2016 | Djupesland |
| 2016/0263334 A1 | 9/2016 | Djupesland |
| 2016/0279357 A1 | 9/2016 | Djupesland |
| 2016/0310683 A1 | 10/2016 | Djupesland et al. |
| 2016/0331916 A1 | 11/2016 | Djupesland et al. |
| 2016/0367771 A1 | 12/2016 | Djupesland |
| 2016/0367772 A1 | 12/2016 | Djupesland |
| 2016/0367774 A1 | 12/2016 | Djupesland et al. |
| 2017/0043108 A1 | 2/2017 | Djupesland et al. |
| 2017/0151397 A1 | 6/2017 | Djupesland |
| 2017/0203061 A1 | 7/2017 | Djupesland et al. |
| 2017/0216540 A1 | 8/2017 | Djupesland |
| 2017/0274164 A1 | 9/2017 | Djupesland et al. |
| 2017/0333649 A1 | 11/2017 | Djupesland |

FOREIGN PATENT DOCUMENTS

| | | |
|---|---|---|
| GB | 1262085 | 2/1972 |
| WO | WO 96/22802 | 8/1996 |
| WO | WO 98/53869 | 12/1998 |
| WO | WO 00/51672 | 9/2000 |
| WO | WO 01/24857 A1 | 4/2001 |
| WO | WO 01/85097 A2 | 11/2001 |
| WO | WO 01/97689 | 12/2001 |
| WO | WO 02/13896 A1 | 2/2002 |
| WO | WO 02/068029 | 9/2002 |
| WO | WO 02/068030 | 9/2002 |
| WO | WO 02/068031 | 9/2002 |
| WO | WO 02/068032 | 9/2002 |
| WO | WO 03/000310 | 1/2003 |
| WO | WO 03/011708 A1 | 2/2003 |
| WO | WO 03/020350 | 3/2003 |
| WO | WO 03/045483 A2 | 6/2003 |
| WO | WO 03/082393 | 10/2003 |
| WO | WO 03/084591 | 10/2003 |
| WO | WO 03/090812 | 11/2003 |
| WO | WO 2004/004814 | 1/2004 |
| WO | WO 2004/004922 | 1/2004 |
| WO | WO 2004/060433 | 7/2004 |
| WO | WO 2004/103447 | 12/2004 |
| WO | WO 2005/016423 | 2/2005 |
| WO | WO 2005/021059 | 3/2005 |
| WO | WO 2006/030210 | 3/2006 |
| WO | WO 2006/090149 | 8/2006 |
| WO | WO 2007/083073 | 7/2007 |
| WO | WO 2007/093784 | 8/2007 |
| WO | WO 2007/093791 | 8/2007 |
| WO | WO 2007/099361 | 9/2007 |
| WO | WO 2007/102089 | 9/2007 |
| WO | WO 2007/107887 | 9/2007 |
| WO | WO 2007/125318 | 11/2007 |
| WO | WO 2007/141541 | 12/2007 |
| WO | WO 2008/012531 | 1/2008 |
| WO | WO 2008/065403 | 6/2008 |
| WO | WO 2008/081326 | 7/2008 |
| WO | WO 2008/081327 | 7/2008 |
| WO | WO 2008/122791 | 10/2008 |
| WO | WO 2008/122795 | 10/2008 |
| WO | WO 2009/044172 | 4/2009 |
| WO | WO 2010/029441 | 3/2010 |
| WO | WO 2012/035427 | 3/2012 |
| WO | WO 2012/123819 | 9/2012 |
| WO | WO 2013/124491 | 8/2013 |
| WO | WO 2013/124492 | 8/2013 |
| WO | WO 2013/124493 | 8/2013 |
| WO | WO 2014/155192 | 10/2014 |

OTHER PUBLICATIONS

English-Language Abstract of WO 02/13896 A1.
English-Language Abstract of EP 1 220 700 B1.
Cindy H. Dubin, *Nothing to Sneeze At*, Pharmaceutical Formulation & Quality Magazine (Jan. 29, 2003).
Per Gisle Djupesland, *Nasal Delivery of Vaccines*, EPC (Jan. 29, 2003).
Per Gisle Djupesland, *Who Nose How Far Nasal Delivery Can Go?*, EPC (Oct. 7, 2003).
Per Gisle Djupesland, *Bi-directional Nasal Drug Delivery*, Innovations in Pharmaceutical Technology (Jul. 10, 2004).
P.G. Djupesland, *Bi-Directional Nasal Delivery of Aerosols Can Prevent Lung Deposition*, Journal of Aerosol Medicine (Sep. 2004).
*Bi-Directional Nasal Device Delivers Drug on Exhalation*, Pharmaceutical Technology (Sep. 10, 2004).
Ola Dale et al., *Intranasal Midazolam: A Comparison of Two Delivery Devices in Human Volunteers*, Journal of Pharmacy and Pharmacology (Oct. 2004).
G. Furness, *Nasal Drug Delivery: Rapid Onset Via A Convenient Route*, ONdrugDelivery Ltd. (2005).
M. Kleven, *Using Computational Fluid Dynamics (CFD) to Improve the Bi-Directional Nasal Drug Delivery Concept*, Trans IChemE Part C. (Jun. 2005).
Per Gisle Djupesland, *Breath-Actuated Bi-Directional Delivery Sets the Nasal Market on a New Course*, ONdrugDelivery (Oct. 10, 2005).
Hilde Bakke et al., *Oral Spray Immunization May be an Alternative to Intranasal Vaccine Delivery to Induce Systemic Antibodies But Not Nasal Mucosal or Cellular Immunity*, Scan J. of Immunol. (Mar. 2006).
P.G. Djupesland et al., *Breath Actuated Nasal Device Improves Delivery to Target Sites Beyond the Nasal Valve*, The Laryngoscope (Mar. 2006).
R. Luthringer et al., Rapid Absorption of Sumatriptan Powder and Effects on Glyceryl tinitrate Model of Headache Following Intranasal Delivery Using a Novel Bi-Directional Device, Journal of Pharmacy and Pharmacology (Jan. 2009).
A. Skretting et al., *A New Method for Scintigraphic Quantification of Deposition and Clearance in Anatomical Regions of the Human Nose*, Nuclear Medicine Communications (Aug. 2009).
Vlckovia et al., *Effective Treatment of Mild-to-Moderate Nasal Polyposis with Fluticasone Delivered by a Novel Device*, Rhinology (Oct. 22, 2009).
Per Gisle Djupesland et al., *Impact of Baseline Nasal Polyp Size and Previous Surgery on Efficacy of Fluticasone Delivered With a Novel Device: A Subgroup Analysis*, Am. J. Rhinology Allergy (2010).

(56) References Cited

OTHER PUBLICATIONS

P.G. Djupesland et al., *Intranasal Sumatriptan Powder Delivered by a Novel Breath Actuated Bi-Directional Device for the Acute Treatment of Migraine: A Randomised Placebo-Controlled Study*, Cephalalgia (Mar. 17, 2010).

F.S. Hansen et al., *Preliminary Efficacy of Fluticasone Delivered By a Novel Device in Recalcitrant Chronic Rhinosinusitis*, Rhinology (Jun. 26, 2010).

Per Gisle Djupesland, *Nasal Drug Delivery Devices: Characteristics and Performance in Clinical Perspective—A Review*, Drug. Deliv. and Transl. Res. (Oct. 18, 2012).

Per Gisle Djupesland, Nasal Deposition and Clearance in Man: Comparison of a Bidirectional Powder Device and a Traditional Liquid Spray Pump, Journal of Aerosol Medicine and Pulmonary Drug Delivery (Nov. 2012).

Stewart J. Tepper, *Clinical Implications for Breath-Powered Powder Sumatriptan Intranasal Treatment*, Headache, The American Headache Society (Apr. 29, 2013).

Mohammad Obaidi et al., *Improved Pharmacokinetics of Sumatriptan With Breath Powered Nasal Delivery of Sumatriptan Powder*, Headache, The American Headache Society (May 24, 2013).

Per Gisle Djupesland, *Breath Powdered Nasal Delivery: A New Route to Rapid Headache Relief*, Headache, The American Headache Society (Jun. 4, 2013).

Per Gisle Djupesland et al., *The Nasal Approach to Delivering Treatment for Brain Diseases: An Anatomic, Physiologic, and Delivery Technology Overview*, Therapeutic Delivery (2014).

R.K. Cady et al., *A Randomized Double-Blind, Placebo Controlled Study of Breath Powered Nasal Delivery of Sumatriptan Powder (AVP-825) in the Treatment of Acute Migraine (The TARGET Study)*, Headache (Sep. 8, 2014).

S.J. Tepper et al., *AVP-825 Breath-Powdered Intranasal Delivery System Containing 22 mg Sumatriptan Powder vs. 100 mg Oral Sumatripta in the Acute Treatment of Migraines (The Compass Study): A Comparative Randomized Clinical Trial Across Multiple Attacks*, Headache: The Journal of Head and Face Pain (Mar. 29, 2015).

D. S. Quintana et al., *Low-dose Oxytocin Delivered Intranasally with Breath Powdered Device Affects Social-Cognitive Behavior: A Randomized Four-Way Crossover Trial with Nasal Cavity Dimension Assessment*, Transl Psychiatry (Jul. 14, 2015).

R. Mahmoud, *Breathe Out*, Innovations in Phar, Tech. (Dec. 10, 2015).

* cited by examiner

DELIVERY DEVICES

This application is a continuation of U.S. patent application Ser. No. 14/456,767, filed, Aug. 11, 2014, which is a continuation of U.S. patent application Ser. No. 10/570,034, filed Dec. 6, 2006, now U.S. Pat. No. 8,800,555, which is the National Phase Application of International Application No. PCT/IB04/03004, filed Aug. 29, 2004, which claims the benefit of and priority to GB 0320171.2 filed on Aug. 28, 2003; the entire contents of each of which are incorporated by reference in their entireties.

The present invention relates to a delivery device for and a method of delivering substance, in particular the delivery of substance as a vapor or a fine aerosol mist, especially containing a medicament, such as systemic or topical pharmaceuticals, or a vaccine, and in particular to the nasal airway of a subject.

Referring to FIG. 34, the nasal airway 1 comprises the two nasal cavities separated by the nasal septum, which airway 1 includes numerous ostia, such as the paranasal sinus ostia 3 and the tubal ostia 5, and olfactory cells, and is lined by the nasal mucosa. The nasal airway 1 can communicate with the nasopharynx 7, the oral cavity 9 and the lower airway 11, with the nasal airway 1 being in selective communication with the anterior region of the nasopharynx 7 and the oral cavity 9 by opening and closing of the oropharyngeal velum 13. The velum 13, which is often referred to as the soft palate, is illustrated in solid line in the closed position, as achieved by providing a certain positive pressure in the oral cavity 9, such as achieved on exhalation through the oral cavity 9, and in dashed line in the open position.

There are many nasal conditions which require treatment. One such condition is nasal inflammation, specifically rhinitis, which can be allergic or non-allergic and is often associated with infection and prevents normal nasal function. By way of example, allergic and non-allergic inflammation of the nasal airway can typically effect between 10 and 20% of the population, with nasal congestion of the erectile tissues of the nasal concha, lacrimation, secretion of watery mucus, sneezing and itching being the most common symptoms. As will be understood, nasal congestion impedes nasal breathing and promotes oral breathing, leading to snoring and sleep disturbance. Other nasal conditions include nasal polyps which arise from the paranasal sinuses, hypertrophic adenoids, secretory otitis media, sinus disease and reduced olfaction.

In the treatment of certain nasal conditions, the topical administration of medicaments is preferable, particularly where the nasal mucosa is the prime pathological pathway, such as in treating or relieving nasal congestion. Medicaments that are commonly topically delivered include decongestants, anti-histamines, cromoglycates, steroids and antibiotics. At present, among the known anti-inflammatory pharmaceuticals, topical steroids have been shown to have an effect on nasal congestion. Topical decongestants have also been suggested for use in relieving nasal congestion. The treatment of hypertrophic adenoids and chronic secretory otitis media using topical decongestants, steroids and anti-microbial agents, although somewhat controversial, has also been proposed. Further, the topical administration of pharmaceuticals has been used to treat or at least relieve symptoms of inflammation in the anterior region of the nasopharynx, the paranasal sinuses and the auditory tubes.

Medicaments can also be systemically delivered through the nasal pathway, the nasal pathway offering a good administration route for the systemic delivery of pharmaceuticals, such as hormones, for example, oxytocin and calcitonin, and analgetics, such as anti-migraine compositions, as the high blood flow and large surface area of the nasal mucosa advantageously provides for rapid systemic uptake.

Nasal delivery is also expected to be advantageous for the administration of medicaments requiring a rapid onset of action, for example, analgetics, anti-emetics, insulin, anti-epileptics, sedatives and hypnotica, and other pharmaceuticals, for example, cardio-vascular drugs. It is envisaged that nasal administration will provide for a fast onset of action, at a rate similar to that of injection and at a rate much faster than that of oral administration. Indeed, for the treatment of many acute conditions, nasal administration is advantageous over oral administration, since gastric stasis can further slow the onset of action following oral administration.

It is also expected that nasal delivery could provide an effective delivery route for the administration of proteins and peptides as produced by modern biotechnological techniques. For such substances, the metabolism in the Intestines and the first-pass-effect in the liver represent significant obstacles for reliable and cost-efficient delivery.

Furthermore, it is expected that nasal delivery using the nasal delivery technique of the present invention will prove effective in the treatment of many common neurological diseases, such as Alzheimer's, Parkinson's, psychiatric diseases and Intracerebral infections, where not possible using existing techniques. The nasal delivery technique of the present invention allows for delivery to the olfactory region, which region is located in the superior region of the nasal cavities and represents the only region where it is possible to circumvent the blood-to-brain barrier (BBB) and enable communication with the cerebrospinal fluid (CSF) and the brain.

Also, it is expected that the nasal delivery technique of the present invention will allow for the effective delivery of vaccines.

Aside from the delivery of medicaments, the irrigation of the nasal mucosa with liquids, in particular saline solutions, is commonly practised to remove particles and secretions, as well as to improve the mucociliary activity of the nasal mucosa. These solutions can be used in combination with active pharmaceuticals.

To date, nasal medicaments have been primarily delivered as drops or by mechanical nasal spray pumps.

It is an aim of the present invention to provide an Improved delivery device and method for delivering substance, in particular, though not exclusively to the nasal airway of subjects.

In one aspect the present invention provides a delivery device, comprising: an outlet member through which substance is in use delivered in an entraining gas flow; and a substance supply unit for supplying substance to be entrained by an entraining gas flow as one or both of a vapor or a fine aerosol mist, wherein the substance supply unit comprises a flow channel which is fluidly connected to the outlet member, and a substance supporting element for supporting substance, at least a surface of which is in use disposed in the flow channel.

In one embodiment the delivery device further comprises: a mouthpiece which is fluidly connected to the flow channel of the substance supply unit, whereby exhalation into the mouthpiece by a user acts to generate the entraining gas flow.

In one embodiment the mouthpiece comprises a flexible member which is such as to allow for movement to an operative position.

Preferably, the mouthpiece comprises an extendable member which has a first, collapsed state and a second, operative extended state.

More preferably, the mouthpiece comprises a concertinaed member.

In another embodiment the delivery device further comprises: a gas supply unit which is fluidly connected to the flow channel of the substance supply unit, the gas supply unit being actuatable to deliver the entraining gas flow on actuation thereof.

In one embodiment the gas supply unit is a manually-actuated unit.

In another embodiment the gas supply unit is a breath-actuated unit.

In one embodiment the flow channel includes a chamber.

In another embodiment the flow channel includes an elongate channel.

Preferably, the substance supporting element comprises an elongate element extending along a length of the flow channel.

In one embodiment the substance supporting element comprises a body which encloses the flow channel and Includes a plurality of flow passages therethrough, such that the entraining gas flow is forced through the flow passages and thereby entrains substance from the substance supporting element.

In another embodiment the substance supporting element comprises a body which is disposed in the flow channel, such that the entraining gas flow flows thereover and thereby entrains substance from the substance supporting element.

In a further embodiment the substance supporting element comprises a porous element which is disposed in the flow channel, such that the entraining gas flow flows therethrough and thereby entrains substance from the substance supporting element.

In yet another embodiment the substance supporting element comprises a porous, capillary element which is loadable with substance and configured to present substance at the capillaries at the surface of the substance supporting element in the flow channel for entrainment by the entraining gas flow.

Preferably, the substance supporting element is configured such that application of a pressure to another surface of the substance supporting element causes substance to be delivered from the capillaries to the surface of the substance supporting element in the flow channel for entrainment by the entraining gas flow.

In a yet further embodiment the flow channel comprises a first, upstream flow channel section into which the entraining gas flow is in use delivered, a second, downstream flow channel section, and a flow resistor fluidly connecting the upstream and downstream flow channel sections, with the flow resistor providing a predeterminable flow resistance to the entraining gas flow and thereby developing a predeterminable pressure in the upstream flow channel section, and the substance supporting element comprises a porous, capillary element which is loadable with substance and disposed such that a first, pressure surface thereof defines a part of the upstream flow channel section and a second, delivery surface thereof defines a part of the downstream flow channel section, whereby the developed pressure in the upstream flow channel section acts to pressurize the pressure surface of the substance supporting element, which pressure in turn acts to drive substance through the capillaries and to the delivery surface of the substance supporting element, and the entraining gas flow passing through the flow resistor and the downstream flow channel section acts to entrain substance presented at the delivery surface of the substance supporting element in the downstream flow channel section.

In still another embodiment the substance supply unit comprises a substance supporting unit which comprises a movable member which is movable by the entraining gas flow as delivered though the flow channel, and the substance supporting element which is disposed to the movable member such as to be moved with the same.

Preferably, the substance supporting element comprises a capillary structure which is loadable with substance, and, on movement of the substance supporting element, substance is driven outwardly to an outer surface of the substance supporting element, which substance presented at the capillaries is in use entrained by the entraining gas flow.

Preferably, the movable member is a rotatable member which is rotatable by the entraining gas flow as delivered though the flow channel.

In one embodiment the substance supply unit further comprises a substance dosing unit for dosing the substance supporting element with substance.

Preferably, the substance dosing unit is configured to deliver a predeterminable dose of substance.

In one embodiment the substance dosing unit comprises a blister element which contains substance and comprises a body member and a closure member which normally closes the body member, with the closure member being ruptured on depressing the body member to release substance contained therein.

Preferably, the substance dosing unit comprises a blister pack member which includes a plurality of blister elements which each contain substance and comprise a body member and a closure member which normally closes the body member, with the closure member being ruptured on depressing the body member to release substance contained therein, such as to provide for successive dosing of the substance supporting element with substance by use of successive ones of the blister elements.

In one embodiment the flow channel includes a delivery port and comprises first and second channel sections, the respective ends of which terminate at the delivery port, such that in use the entraining gas flow is directed through the first channel section into a blister element which is located at the delivery port.

In another embodiment the substance dosing unit comprises a cartridge which contains substance and is openable to enable release of the contained substance.

Preferably, the cartridge comprises a body and at least one closure member which normally closes the body and is ruptured to enable release of the contained substance.

More preferably, the cartridge comprises a tubular body and closure elements at the respective ends of the tubular body which normally close the body and are ruptured to enable release of the contained substance by delivery of the entraining gas flow therethrough.

Still more preferably, the tubular body is a flexible body which is configured such that, on squeezing the tubular body diametrally, the closure elements are ruptured.

Preferably, the cartridge includes the substance supporting element therewithin.

In a further embodiment the substance dosing unit comprises a reservoir for containing a volume of substance and is operably fluidly connected to the substance supporting element such as to deliver a dose of substance to the substance supporting element on each actuation thereof.

Preferably, the reservoir is such as to reduce in volume on each actuation thereof.

Preferably, the substance supply unit comprises an Inlet closure member which normally closes an Inlet and of the flow channel, and Is openable on delivery of the entraining gas flow.

In one embodiment the Inlet closure member comprises a one-way valve which is opened on delivery of the entraining gas flow.

In another embodiment the Inlet closure member comprises a closure member which is ruptured on delivery of the entraining gas flow.

Preferably, the substance supply unit comprises an outlet closure member which normally closes an outlet end of the flow channel, and is openable on delivery of the entraining gas flow.

In one embodiment the outlet closure member comprises a one-way valve which is opened on delivery of the entraining gas flow.

In another embodiment the outlet closure member comprises a closure member which is ruptured on delivery of the entraining gas flow.

In one embodiment the delivery device further comprises: a flow control unit for controlling an extent of exhalation through the delivery device, such as to provide for delivery of a predeterminable dose of substance.

Preferably, the flow control unit comprises a shaft, a movable member which is disposed to the shaft such as to be driven by the exhalation gas flow between a first, open position, which permits delivery of the exhalation gas flow through the flow channel, and a second, closed position, and a stop member, against which the movable member is disposed when in the closed position, such as at least substantially to prevent further delivery of the exhalation air flow through the flow channel.

In one embodiment the outlet member comprises an inlet nosepiece for fitting to a nostril of the user.

Preferably, the delivery device further comprises: an outlet unit for fitting to the other nostril of the user, wherein the outlet unit comprises an outlet nosepiece for fitting to the other nostril of the user and a flow resistor fluidly connected to the outlet nosepiece such as to provide a flow resistance to the entraining gas flow where delivered through the nasal airway of the user.

In one embodiment the substance comprises a vapor.

In another embodiment the substance comprises a liquid which is delivered as a fine liquid aerosol mist.

In a further embodiment the substance comprises a powder which is delivered as a fine powder aerosol mist.

In one embodiment the substance comprises a decongestant.

In another aspect the present invention provides a delivery device, comprising: an outlet member through which substance is in use delivered in an entraining gas flow; and a substance supply unit for supplying substance to be entrained by an entraining gas flow as one or both of a vapor or a fine aerosol mist, wherein the substance supply unit comprises a flow channel which is fluidly connected to the outlet member through which the entraining gas flow is in use delivered and defines a receiving chamber for receiving a substance dosing unit.

Preferably, the substance dosing unit comprises a cartridge which contains substance and is openable to enable release of the contained substance.

More preferably, the cartridge includes a substance supporting element for supporting substance therewithin.

Preferably, the cartridge comprises a body and at least one closure member which normally closes the body and is ruptured to enable release of the contained substance.

More preferably, the cartridge comprises a tubular body and closure elements at the respective ends of the tubular body which normally close the tubular body and are ruptured to enable release of the contained substance, with the receiving chamber and the cartridge being configured such that the cartridge is disposed such that the entraining gas flow is delivered through the tubular body.

Preferably, the substance supply unit further comprises a dosing member which is movable between a first, open position which allows for introduction of a substance dosing unit into the receiving chamber and a second, closed position which encloses the receiving chamber.

More preferably, the tubular body is a flexible body which is configured such that, on squeezing the tubular body diametrally, the closure elements are ruptured, and the dosing member is configured to squeeze the tubular body when moved to the closed position.

In a further aspect the present invention provides a cartridge which contains substance to be entrained by an entraining gas flow as one or both of a vapor or a fine aerosol mist, with the cartridge being openable to enable release of the contained substance.

Preferably, the cartridge includes a substance supporting element for supporting substance therewithin.

Preferably, the cartridge comprises a body and at least one closure member which normally closes the body and is ruptured to enable release of the contained substance.

More preferably, the cartridge comprises a tubular body and closure elements at the respective ends of the tubular body which normally close the tubular body and are ruptured to enable release of the contained substance.

Still more preferably, the tubular body is a flexible body which is configured such that, on squeezing the tubular body diametrally, the closure elements are ruptured.

In a still further aspect the present invention provides a method of delivering substance, comprising the steps of: providing a substance supporting element in a flow channel; and delivering an entraining gas flow through the flow channel to entrain substance, as one or both of a vapor or a fine aerosol mist, from the substance supporting element.

In its preferred embodiment, the closure of the oropharyngeal velum during the delivery of substance to the nasal airway prevents the possible inhalation of substance, thereby enabling the delivery of fine aerosol mists having a much smaller mean particle size than achieved by traditional nasal spray pumps. In this way, an aerosol mist can be generated which has an optimal particle size distribution. In this regard, the droplets preferably have a mean particle size of less than about 10 μm, more preferably less than about 5 μm, and yet more preferably less than about 1 μm.

In addition, the applicant has recognized that, by establishing a bi-directional flow through the nasal cavities as described in WO-A-00/51672, that is, a flow can be developed which passes into one nostril, around the posterior margin of the nasal septum and in the opposite direction out of the other nostril. Such bi-directional flow also advantageously acts to stimulate the sensory nerves in the nasal mucosa, thereby conditioning the subject for the delivery and providing a more comfortable delivery situation. A yet further advantage is that the bi-directional flow acts to create a positive pressure inside the nasal passages connected in series, which tends to expand and widen narrow and congested regions.

Furthermore, in its preferred embodiment the delivery device does not require the application of an actuation force by the subject at the time of use. Traditionally, mechanical liquid delivery pumps are operated by the manual compression of a chamber containing a volume of liquid to expel a flow of a metered volume of liquid, and mechanical powder delivery pumps are operated by the manual compression of a chamber containing a volume of air to drive and expel a flow of a metered amount of a dry powder. Such operation requires a relatively high actuation force, typically of the order of 50 N, which high force often leads to significant movement of the delivery device, it being very difficult to maintain a delivery device stationary when attempting to apply a high actuation force. Movement of the delivery device, both in the positioning and orientation of the nozzle, will lead to poor reproducibility, dose accuracy and patient compliance.

Yet furthermore, in providing for the closure of the oropharyngeal velum of a subject, substance is prevented from entering the lower airway, and also, in a preferred embodiment, bi-directional delivery can be achieved through the nasal cavities.

Preferred embodiments of the present invention will now be described hereinbelow by way of example only with reference to the accompanying drawings, in which.

Figure 34:
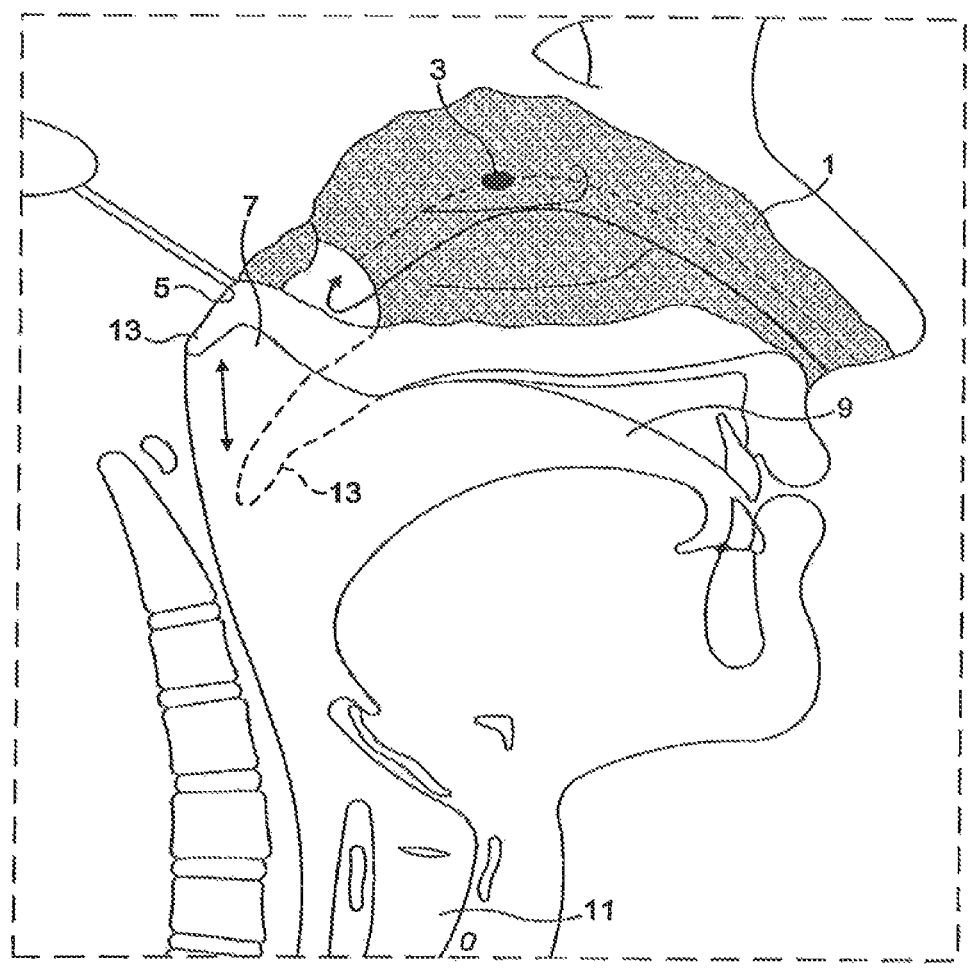

FIG. 34 schematically illustrates the anatomy of the upper respiratory tract of a human subject.

Figure 1:
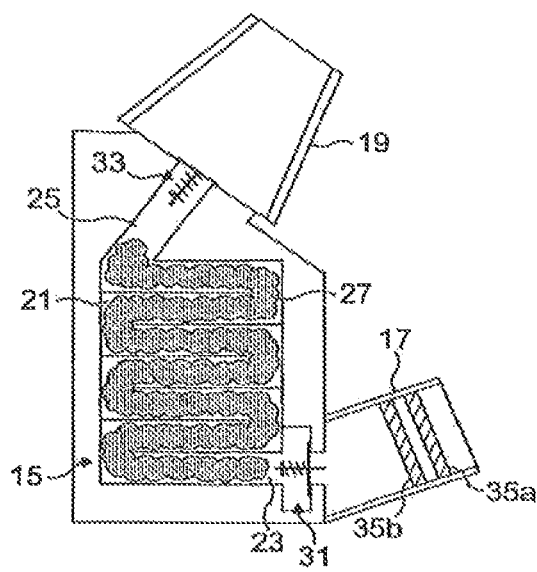
FIG. 1 illustrates a nasal delivery device in accordance with a first embodiment of the present invention.
Figure 2:
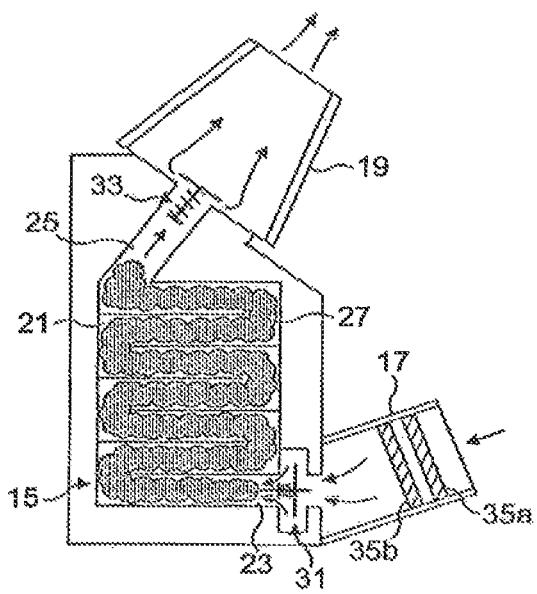
FIG. 2 illustrates the delivery device of FIG. 1 in the operative state.
Figure 3:
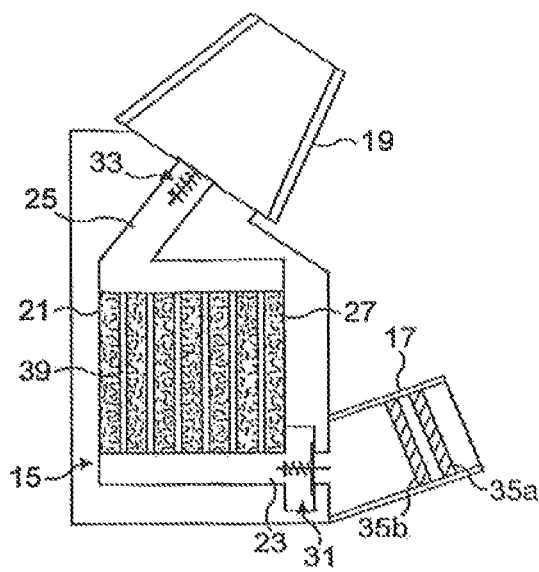
FIG. 3 illustrates a nasal delivery device in accordance with a second embodiment of the present invention.
Figure 4:
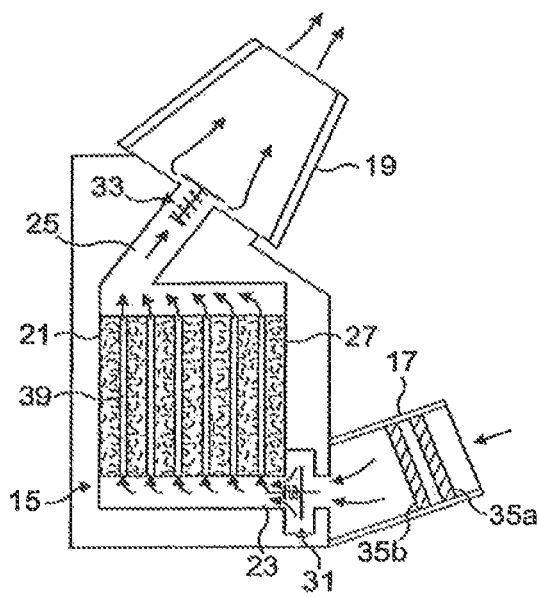
FIG. 4 illustrates the delivery device of FIG. 3 in the operative state.
Figure 5:
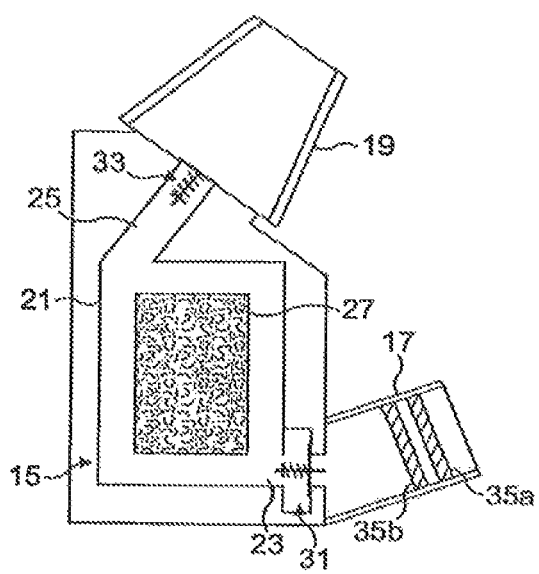
FIG. 5 illustrates a nasal delivery device in accordance with a third embodiment of the present invention.
Figure 6:
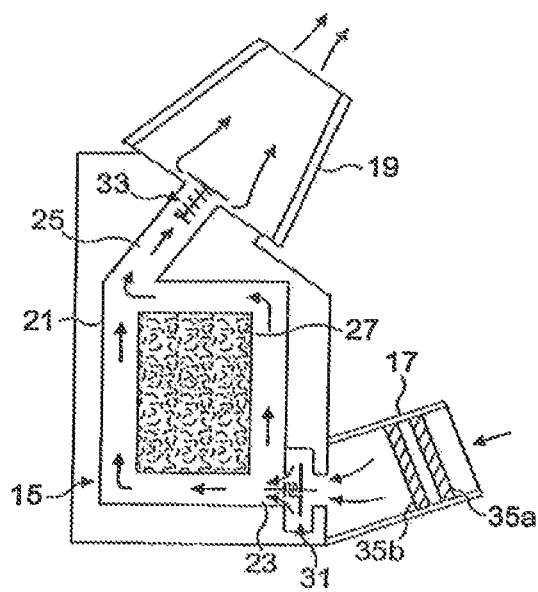
FIG. 6 illustrates the delivery device of FIG. 5 in the operative state.
Figure 7:
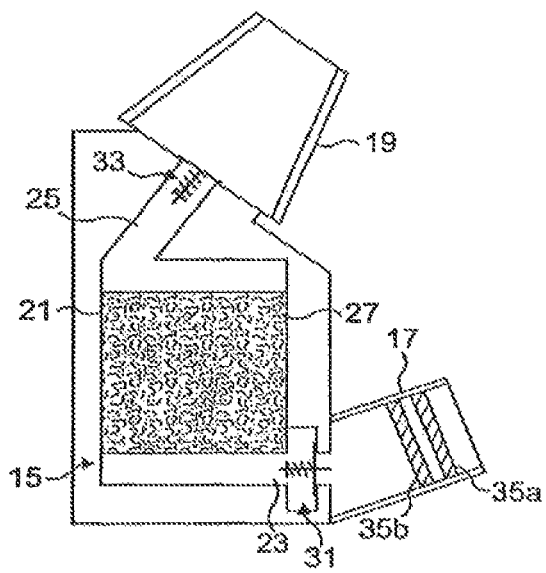
FIG. 7 illustrates a nasal delivery device in accordance with a fourth embodiment of the present invention.
Figure 8:
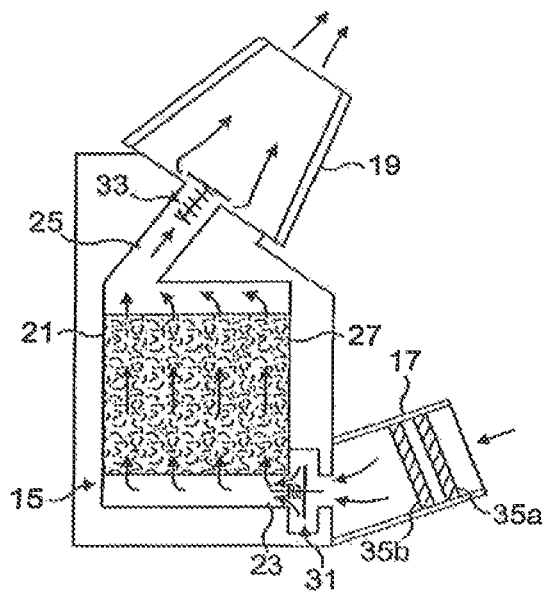
FIG. 8 illustrates the delivery device of FIG. 7 in the operative state.
Figure 9:
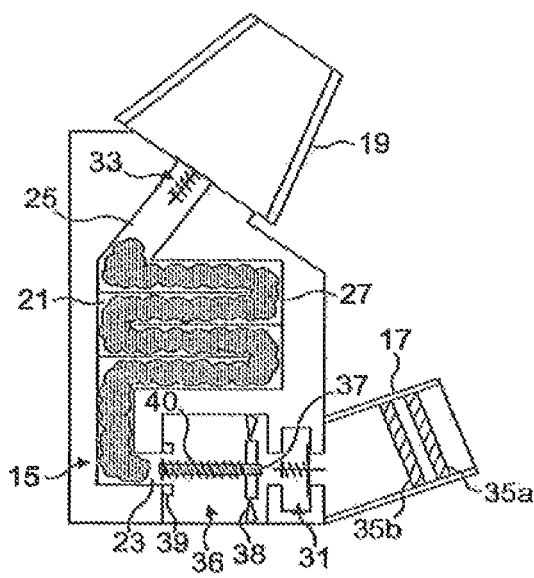
FIG. 9 illustrates a nasal delivery device in accordance with a fifth embodiment of the present invention.
Figure 10:
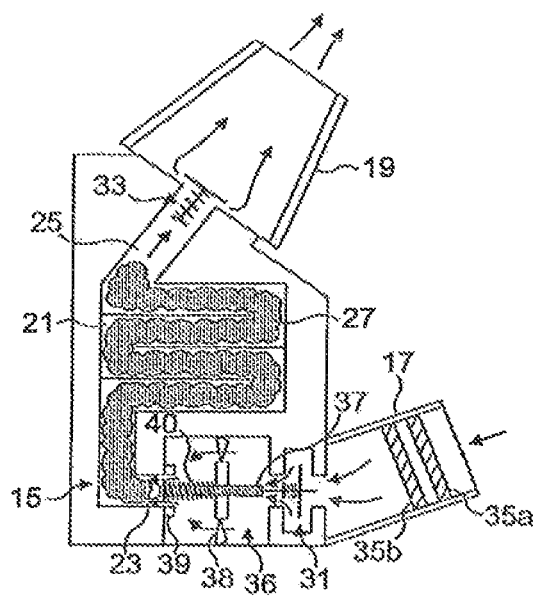
FIG. 10 illustrates the delivery device of FIG. 9 in a first operative state.

FIGS. 1 and 2 illustrate a nasal delivery device in accordance with a first embodiment of the present invention.

The delivery device comprises a substance supply unit 15 containing substance, in this embodiment a decongestant, such as oxymetazoline and xylometazoline, to be delivered as one or both of a vapor or a fine aerosol mist, a mouthpiece 17 through which the user exhales and which is fluidly connected to the substance supply unit 15 such as to cause substance to be entrained by an exhaled air flow, and a nosepiece 19 for fitting to a nostril of the user which is fluidly connected to the substance supply unit 15 such that an air flow entraining the substance is delivered to the nasal airway of the user.

The substance supply unit 15 comprises a flow channel 21, one, inlet end 23 of which is fluidly connected to the mouthpiece 17 and the other, outlet end 25 of which is fluidly connected to the nosepiece 19, and a substance supporting element 27 disposed in the flow channel 21 over which the entraining air flow is directed to entrain substance from the substance supporting element 27.

In this embodiment the flow channel 21 is a tortuous, elongate channel and the substance supporting element 27 is an elongate element which extends along the length of the flow channel 21. With this configuration, the substance supporting element 27 presents a high surface-to-volume ratio and promotes the uptake of substance by the entraining air flow. In a preferred embodiment the flow channel 21 comprises a helical channel.

In other embodiments the flow channel 21 could have any shape or configuration, and the substance supporting element 27 need not encompass the flow channel 21. In one embodiment the substance supporting element 27 could be located at the outlet end 25 of the flow channel 21. Such a configuration can be advantageous where the delivery of a fine aerosol mist is required, as the droplets of the aerosol mist do not have to pass through the flow channel 21 and thus do not encounter any surface which can trap the droplets. In another embodiment the substance supporting element 27 could be located at the Inlet end 23 of the flow channel 21. Such a configuration can be advantageous where the delivery predominantly of a vapour is required, as any droplets of an aerosol mist which are generated have to pass through the flow channel 21 and thus are likely to be trapped on a surface of the flow channel 21.

In this embodiment the substance supporting element 27 and the formulation of the substance are such as to provide for sustained substance delivery over a period of time following first operation of the delivery device, thereby providing a device which can be used repeatedly, typically allowing for use over the period of a day.

In other embodiments, by control of the construction of the substance supporting element 27 and the formulation of the substance, the rate of release of the substance, and hence the rate of uptake of the substance in the entraining air flow, can be controlled. For example, the delivery device could be configured as a single-use, vapor delivery device, where the formulation would be volatile, allowing for the uptake of an entire dose of substance in a single use.

The substance supply unit 15 includes a one-way inlet valve 31 at the Inlet end 23 of the flow channel 21 and a one-way outlet valve 33 at the outlet end 25 of the flow channel 21, which valves 31, 33 act normally to dose the flow channel 21 and prevent the escape of substance therefrom, and, on exhalation through the mouthpiece 17, are opened to allow for the delivery of an entraining air flow through the flow channel 21.

The delivery device further comprises at least one filter element 35, in this embodiment disposed in the mouthpiece 17, for filtering the exhaled air flow. In this embodiment the delivery device comprises a first, anti-microbial filter element 35*a* for filtering microbes from the exhaled air flow and a second, drying filter element 35*b* for de-humidifying the exhaled air flow and thereby promoting the uptake of substance through the flow channel 21.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

FIGS. 3 and 4 illustrate a nasal delivery device in accordance with a second embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from the delivery device of the above-described first embodiment in the construction of the substance supply unit 15. In this embodiment the flow channel 21 comprises a chamber and the substance supporting element 27 comprises a block which encloses the flow channel 21 and includes a plurality of flow passages 39 extending therethrough, such that the exhaled air flow is forced through the flow passages 39 and thereby entrains substance from the substance supporting element 27.

FIGS. 5 and 6 illustrate a nasal delivery device in accordance with a third embodiment of the present invention.

The delivery device of this embodiment is very similar to the delivery device of the above-described second embodiment, and thus, in order to avoid unnecessary duplication of description, only the differences will be described in detail.

The delivery device of this embodiment differs from the delivery device of the above-described second embodiment in the construction of the substance supporting element 27. In this embodiment the substance supporting element 27 comprises a single block, over the external surface of which the exhaled air flow is delivered to entrain substance from the substance supporting element 27.

FIGS. 7 and 8 illustrate a nasal delivery device in accordance with a fourth embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from the delivery device of the above-described first embodiment in the construction of the substance supply unit 15. In this embodiment the flow channel 21 comprises a chamber, and the substance supporting element 27 is a porous structure which encloses the flow channel 21 through which the exhaled air flow is delivered to entrain substance from the substance supporting element 27.

FIGS. 9 to 11 illustrate a nasal delivery device in accordance with a fifth embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from the delivery device of the above-described first embodiment in further comprising a flow control unit 36 for controlling the duration of exhalation through the delivery device, such as to provide for the delivery of a predetermined dose of substance.

In this embodiment the flow control unit 36 comprises a shaft 37, a movable member 38, in this embodiment in the form of a propeller, which is threadedly engaged to the shaft 37 such as to be driven by an exhalation air flow between a first, open position, which permits the generation of an exhalation air flow through the flow channel 21, and a second, closed position, a stop member 39 against which the movable member 37 is disposed when in the closed position, such as at least substantially to prevent the generation of an exhalation air flow through the flow channel 21, and a biasing element 40, in this embodiment a resilient element, here a compression spring, which acts to bias the movable member 38 to the open position and against which bias the movable member 38 is driven by an exhalation air flow. With this configuration, the delivery of a predetermined flow volume is required to move the movable member 38 between the first, open position and the second, closed position, at which point an exhalation air flow is not delivered through the flow channel 21. In providing only for the delivery of a predetermined flow volume through the flow channel 21, which corresponds to a predetermined duration at a predetermined flow rate, a predetermined dose of substance is delivered.

In an alternative embodiment the flow control unit 36 could be an electronic unit which includes a valve and a flow meter to measure the flow rate, such as to enable operation of the valve following the delivery of a predetermined flow volume through the flow channel 21.

In another alternative embodiment the flow control unit 36 could be an electronic unit which includes a valve and a timer, such as to enable operation of the valve following the delivery of an exhalation flow through the flow channel 21 for a predetermined period of time.

FIGS. 12 and 13 illustrate a nasal delivery device in accordance with a sixth embodiment of the present invention.

The delivery device of this embodiment is quite similar to the delivery device of the above-described first embodiment, and thus, in order to avoid unnecessary duplication of description, only the differences will be described in detail.

The delivery device of this embodiment differs from the delivery device of the above-described first embodiment in that the delivery device further comprises an outlet unit 59 for fitting to the other nostril of the user.

The outlet unit 59 comprises a nosepiece 61 for fitting to the other nostril of the user and a flow resistor 63 which is fluidly connected to the nosepiece 61 such as to present a flow resistance to the air flow as delivered through the nasal airway of the user.

In this embodiment the flow resistor 63 has a predeterminable fixed resistance which presents a fixed flow resistance to an air flow as delivered through the nasal airway. In an alternative embodiment the flow resistor 63 could be a progressive resistor, such as an Inflatable element, which presents a progressively increasing flow resistance to an air flow as delivered through the nasal airway.

In an alternative embodiment, instead of utilizing an outlet unit 59 in order to provide a flow resistance, the user could simply at least partially occlude his/her other nostril by pressing on the same.

Figure 14:
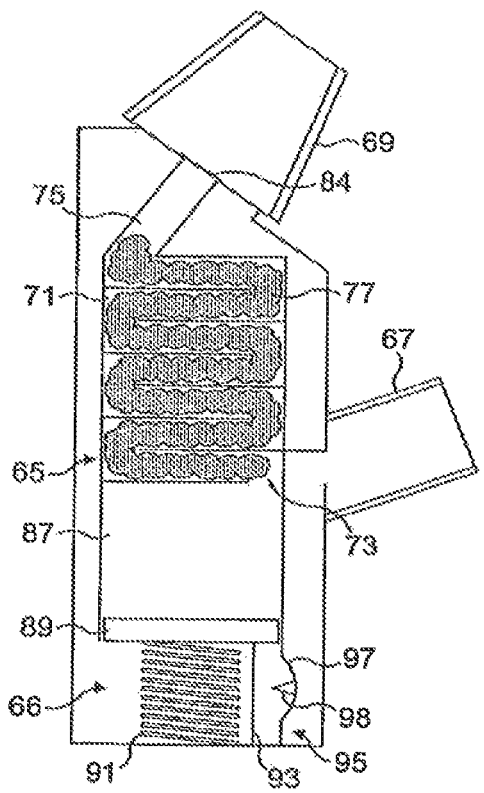
FIG. 14 illustrates a nasal delivery device in accordance with a seventh embodiment of the present invention.
Figure 15:
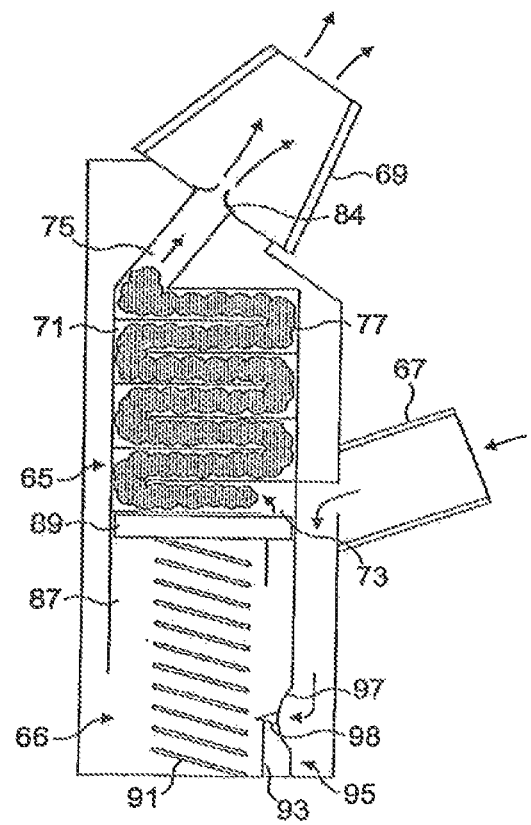
FIG. 15 illustrates the delivery device of FIG. 14 in the operative state.

FIGS. 14 and 15 illustrate a nasal delivery device in accordance with a seventh embodiment of the present invention.

The delivery device comprises a substance supply unit 65 containing substance, in this embodiment a decongestant, to be delivered as one or both of a vapor or a fine aerosol mist, a breath-actuated gas supply unit 66 which is fluidly connected to the substance supply unit 65 and actuatable to deliver a gas flow, separate from the exhalation breath of a user, through the substance supply unit 65, a mouthpiece 67 into which the user exhales to actuate the gas supply unit 66, and a nosepiece 69 for fitting to a nostril of the user which is fluidly connected to the substance supply unit 65 such that the delivered gas flow entraining substance is delivered to the nasal airway of the user.

The substance supply unit 65 comprises a flow channel 71, one, inlet end 73 of which is fluidly connected to the gas supply unit 66 and the other, outlet end 75 of which is fluidly connected to the nosepiece 69, and a substance supporting element 77 disposed in the flow channel 71 over which the entraining gas flow is directed to entrain substance from the substance supporting element 77.

In this embodiment the flow channel 71 is a tortuous, elongate channel and the substance supporting element 77 is an elongate element which extends along the length of the flow channel 71. With this configuration, the substance supporting element 77 presents a high surface-to-volume ratio and promotes the uptake of substance by the entraining gas flow. In one embodiment the flow channel 71 comprises a helical channel.

In other embodiments the flow channel 71 could have any shape or configuration, and the substance supporting element 77 need not encompass the flow channel 71. In one embodiment the substance supporting element 77 could be located at the outlet end 75 of the flow channel 71. Such a configuration can be advantageous where the delivery of a fine aerosol mist is required, as the droplets of the aerosol mist do not have to pass through the flow channel 71 and thus do not encounter any surface which can trap the droplets. In another embodiment the substance supporting element 77 could be located at the Inlet end 73 of the flow channel 71. Such a configuration can be advantageous where the delivery predominantly of a vapour is required, as any droplets of an aerosol mist which are generated have to pass through the flow channel 71 and thus are likely to be trapped on a surface of the flow channel 71.

In this embodiment the delivery device is configured as a single-use, delivery device, and the formulation of the substance is relatively volatile, allowing for the uptake of an entire dose of substance.

The substance supply unit 65 includes a frangible seal element 84 at the outlet end 75 of the flow channel 71, which seal element 84 acts normally to close the flow channel 71 and prevent the escape of substance therefrom, and, on actuation of the gas supply unit 66, is opened to allow for the delivery of the entraining gas flow through the flow channel 71. In this embodiment the seal element 84 is ruptured by the gas flow as generated by the gas supply unit 66.

Figure 11:
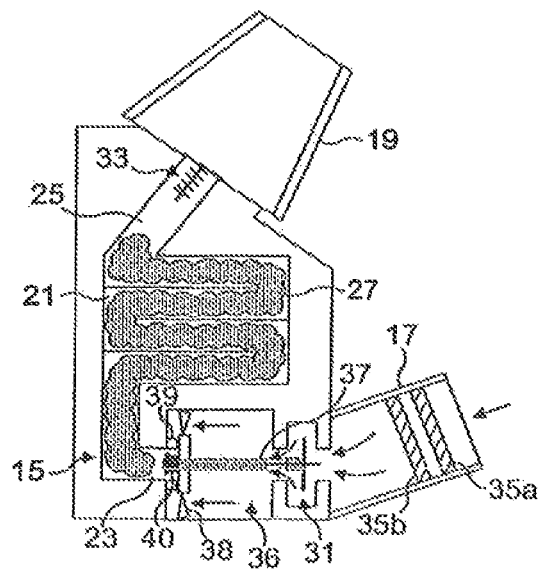
FIG. 11 illustrates the delivery device of FIG. 9 in a second operative state.
Figure 12:
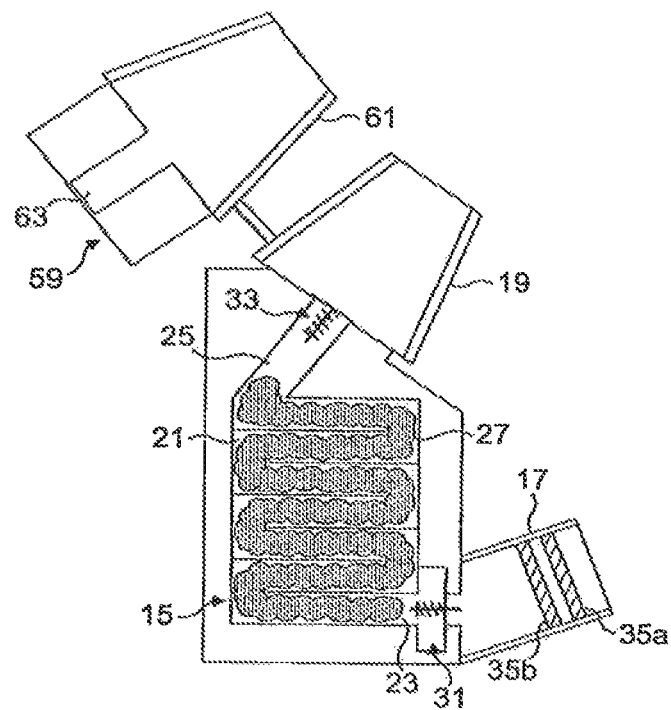
FIG. 12 illustrates a nasal delivery device in accordance with a sixth embodiment of the present invention.
Figure 13:
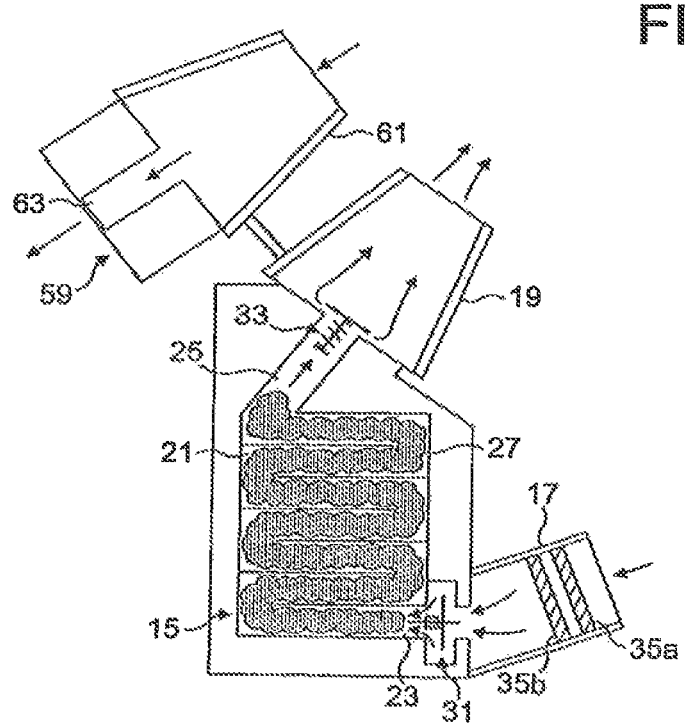
FIG. 13 illustrates the delivery device of FIG. 12 in the operative state.

The gas supply unit 66 comprises a cavity 87 which contains a volume of gas and is fluidly connected to the Inlet end 73 of the flow channel 71, a piston 89 which is slideably disposed in the cavity 87 between a first, non-actuated position, as illustrated in FIG. 11, and a second, actuated position, as illustrated in FIG. 12, in which the volume of gas is driven through the flow channel 71, a biasing element 91, in this embodiment a resilient element, for biasing the piston 89 with a loading force, a restraining element 93 for normally maintaining the piston 89 in the non-actuated position and being configured to release the piston 89 on being broken, and an actuating mechanism 95 for breaking the restraining element 93 on exhalation by the user such as to release the piston 89 and thereby cause the piston 89 to be driven to the actuated position by the loading force as applied thereto by the biasing element 91. In this embodiment the actuating mechanism 95 comprises a flexible diaphragm 97 which is deflected on exhalation by the user and a cutter element 98 which is supported by the diaphragm 97 such as to act to cut the restraining element 93 with deflection of the diaphragm 97 as achieved by exhalation by the user.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 16:
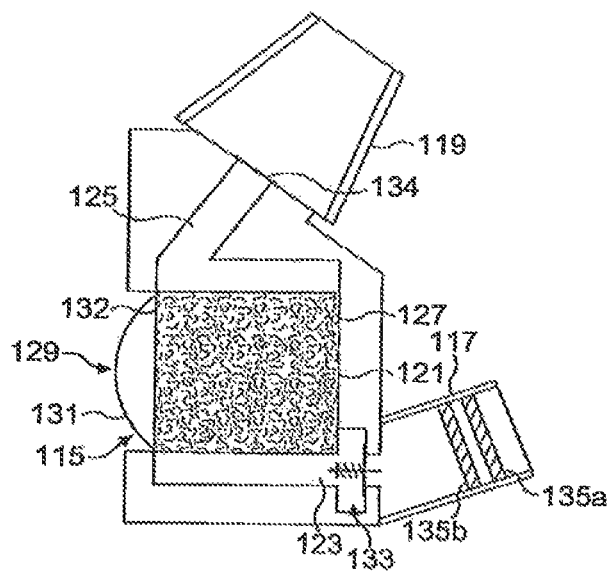
FIG. 16 illustrates a nasal delivery device in accordance with an eighth embodiment of the present invention.
Figure 17:
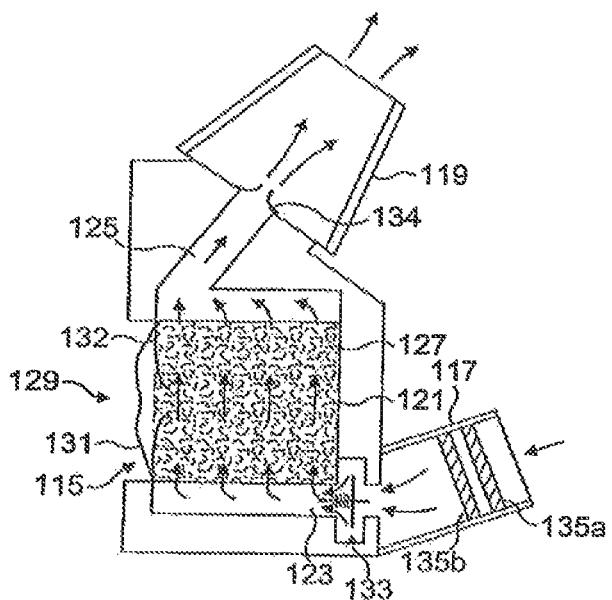
FIG. 17 illustrates the delivery device of FIG. 16 in the operative state.

FIGS. 16 and 17 illustrate a nasal delivery device in accordance with an eighth embodiment of the present invention.

The delivery device comprises a substance supply unit 115 containing substance, in this embodiment a decongestant, to be delivered as one or both of a vapor or a fine aerosol mist, a mouthpiece 117 through which the user exhales and which is fluidly connected to the substance supply unit 115 such as to cause substance to be entrained by an exhaled air flow, and a nosepiece 119 for fitting to a nostril of the user which is fluidly connected to the substance supply unit 115 such that an air flow entraining the substance is delivered to the nasal airway of the user.

The substance supply unit 115 comprises a flow channel 121, in this embodiment a planar chamber, one, inlet end 123 of which is fluidly connected to the mouthpiece 117 and the other, outlet end 125 of which is fluidly connected to the nosepiece 119, and a substance supporting element 127, in this embodiment a porous, absorbent element, which is disposed in the flow channel 121 and over which the entraining air flow is directed to entrain substance from the substance supporting element 127 where dosed with substance, as will be described in more detail hereinbelow.

The substance supply unit 115 further comprises a dosing unit 129 for dosing the substance supporting element 127 with a predetermined dose of substance. In this embodiment the dosing unit 129 comprises a flexible blister element 131 which contains the dose of substance, and a frangible closure element 132 which normally encloses the blister element 131 and Is in fluid communication with the flow channel 121, such that depression of the blister element 131 acts to break the closure element 132 and causes the contained substance to be dosed onto the substance supporting element 127.

In this embodiment the substance supporting element 127 and the formulation of the substance are such as to provide for sustained substance delivery over a period of time following dosing of the substance supporting element 127, thereby providing a device which can be used repeatedly, typically allowing for use over the period of a day.

In other embodiments, by control of the construction of the substance supporting element 127 and the formulation of the substance, the rate of release of the substance, and hence the rate of uptake of the substance in the entraining air flow, can be controlled. For example, the delivery device could be configured as a single-use, vapor delivery device, where the formulation would be volatile, allowing for the uptake of an entire dose of substance in a single use.

The substance supply unit 115 includes a one-way valve 133 at the inlet end 123 of the flow channel 121 and a frangible seal element 134 at the outlet end 125 of the flow channel 121, which valve 133 and seal element 134 act normally to close the flow channel 121 and prevent the escape of substance therefrom, and, on exhalation through the mouthpiece 117, are opened to allow for the delivery of an air flow through the flow channel 121. In this embodiment the seal element 134 is ruptured by the air flow as generated by the exhalation breath of the user.

The delivery device further comprises at least one filter element 135, in this embodiment disposed in the mouthpiece 117, for filtering the exhaled air flow. In this embodiment the delivery device comprises a first, anti-microbial filter element 135*a* for filtering microbes from the exhaled air flow and a second, drying filter element 135*b* for de-humidifying the exhaled air flow and thereby promoting the uptake of substance through the flow channel 121.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 18:
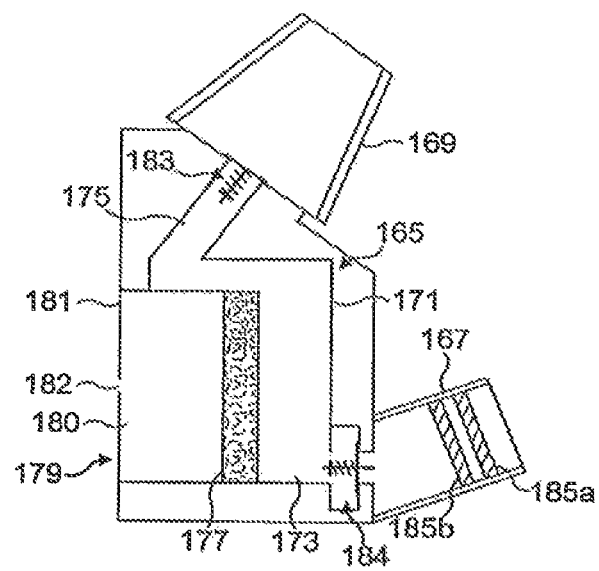
FIG. 18 illustrates a nasal delivery device in accordance with a ninth embodiment of the present invention.
Figure 19:
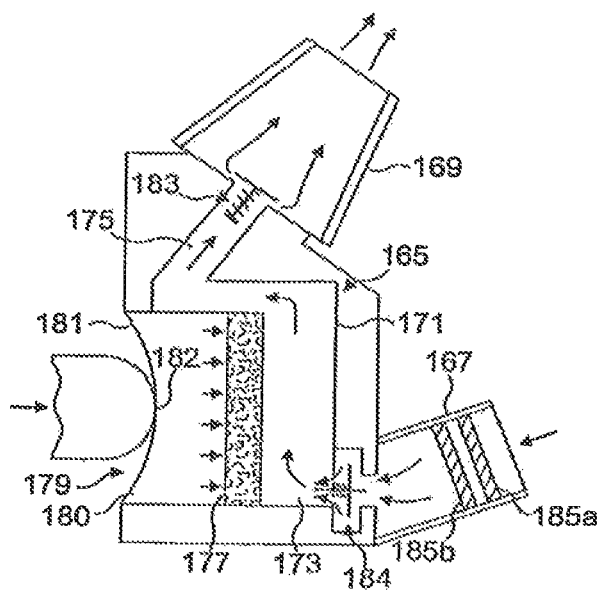
FIG. 19 illustrates the delivery device of FIG. 18 in the operative state.

FIGS. 18 and 19 illustrate a nasal delivery device in accordance with a ninth embodiment of the present invention.

The delivery device comprises a substance supply unit 165 for supplying substance, in this embodiment a decongestant, to be delivered as one or both of a vapor or a fine aerosol mist, a mouthpiece 167 through which the user exhales and which is fluidly connected to the substance supply unit 165 such as to cause substance to be entrained by an exhaled air flow, and a nosepiece 169 for fitting to a nostril of the user which is fluidly connected to the substance supply unit 165 such that an air flow entraining the substance is delivered to the nasal airway of the user.

The substance supply unit 165 comprises a flow channel 171, in this embodiment an elongate channel, one, inlet end 173 of which is fluidly connected to the mouthpiece 167 and the other, outlet and 175 of which is fluidly connected to the nosepiece 169, and a substance supporting element 177 which defines a part of the flow channel 171 and over a delivery surface of which the entraining air flow is directed to entrain substance from the substance supporting element 177 where dosed with substance, as will be described in more detail hereinbelow.

In this embodiment the substance supporting element 177 comprises a porous, capillary element which is loaded with substance and is such that the application of a pressure to another surface, here an opposite, pressure surface, of the substance supporting element 177 causes substance to be delivered from the capillaries to the delivery surface of the substance supporting element 177 for entrainment by the entraining air flow.

The substance supply unit 165 further comprises a dosing unit 179 for dosing substance to the delivery surface of the substance supporting element 177.

In this embodiment the dosing unit 179 comprises a compressible chamber 180 which is in fluid communication with the pressure surface of the substance supporting element 177, with one wall member 181 of the chamber 180 being flexible, here resilient, such that depression of the wall member 181 acts to pressurize the air contained in the chamber 180, which in turn pressurizes the pressure surface of the substance supporting element 177 and drives substance through the capillaries and to the delivery surface of the substance supporting element 177. In this embodiment the wall member 181 includes an aperture 182 which is closed on depressing the wall member 181, typically with a finger or thumb, and opened on releasing the wall member 181 such as to allow for the Introduction of air into the chamber 180 and thereby prevent the substance from being drawn back through the capillaries of the substance supporting element 177.

In an alternative embodiment the dosing unit 179 could comprise a plate which is disposed adjacent the pressure surface of the substance supporting element 177, such that the application of pressure to the plate acts to pressurize the pressure surface of the substance supporting element 177 and drives substance through the capillaries and to the delivery surface of the substance supporting element 177.

With this configuration, the delivery device provides for repeated use until the substance supporting element 177 is exhausted of substance. Thus, by loading the substance supporting element 177 to differing degrees, the delivery device can be configured for use over different periods, for example, daily, weekly, etc.

It is envisaged that this configuration will find particular application in the delivery of a fine aerosol mist, where the substance presented from the capillaries at the delivery surface of the substance supporting element 177 is entrained as droplets, with the dimension of the droplets being determined by the dimension of the capillaries in the substance supporting element 177.

The substance supply unit 165 includes a one-way inlet valve 183 at the Inlet end 173 of the flow channel 171 and a one-way outlet valve 184 at the outlet end 175 of the flow channel 171, which valves 183, 184 act normally to close the flow channel 171 and prevent the escape of substance therefrom, and, on exhalation through the mouthpiece 167, are opened to allow for the delivery of an entraining air flow through the flow channel 171.

The delivery device further comprises at least one filter element 185, in this embodiment disposed in the mouthpiece 167, for filtering the exhaled air flow. In this embodiment the delivery device comprises a first, anti-microbial filter element 185a for filtering microbes from the exhaled air flow and a second, drying filter element 185b for de-humidifying the exhaled air flow and thereby promoting the uptake of substance through the flow channel 171.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 20:
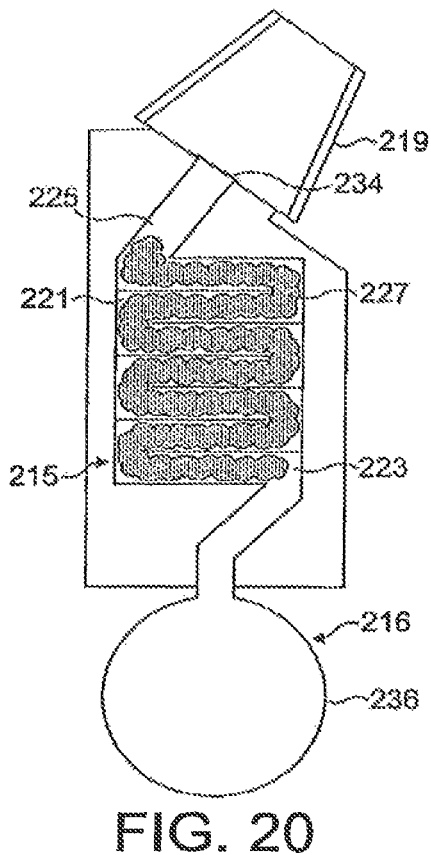
FIG. 20 illustrates a nasal delivery device in accordance with a tenth embodiment of the present invention.
Figure 21:
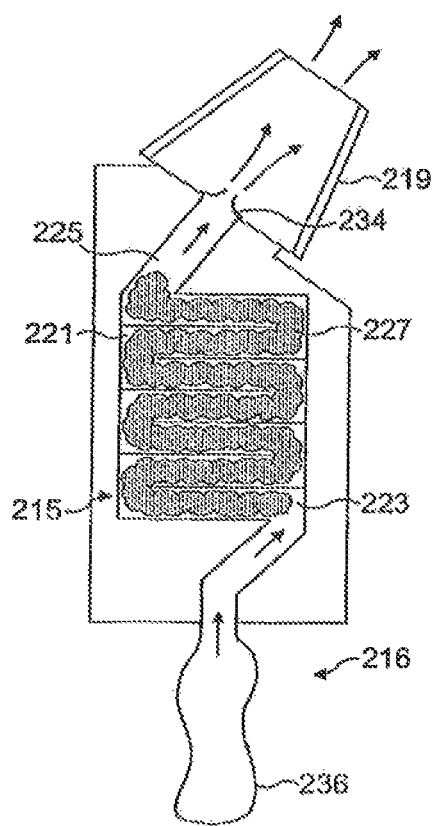
FIG. 21 illustrates the delivery device of FIG. 20 in the operative state.

FIGS. 20 and 21 illustrate a nasal delivery device in accordance with a tenth embodiment of the present invention.

The delivery device comprises a substance supply unit 215 for supplying substance, in this embodiment a decongestant, to be delivered as one or both of a vapor or a fine aerosol mist, a gas supply unit 216 which is fluidly connected to the substance supply unit 215 and operable to deliver a gas flow to the substance supply unit 215, and a nosepiece 219 for fitting to a nostril of the user which is fluidly connected to the substance supply unit 215 such that the gas flow entraining substance is delivered to the nasal airway of the user.

The substance supply unit 215 comprises a flow channel 221, one, inlet end 23 of which is fluidly connected to the gas supply unit 216 and the other, outlet end 225 of which is fluidly connected to the nosepiece 219, and a substance supporting element 227 disposed in the flow channel 21 over which the entraining gas flow is directed to entrain substance from the substance supporting element 227.

In this embodiment the flow channel 221 is a tortuous, elongate channel and the substance supporting element 227 is an elongate element which extends along the length of the flow channel 221. With this configuration, the substance supporting element 227 presents a high surface-to-volume ratio and promotes the uptake of substance by the entraining gas flow. In a preferred embodiment the flow channel 221 comprises a helical channel.

In other embodiments the flow channel 221 could have any shape or configuration, and the substance supporting element 227 need not encompass the flow channel 221. In one embodiment the substance supporting element 227 could be located at the outlet end 225 of the flow channel 221. Such a configuration can be advantageous where the delivery of a fine aerosol mist is required, as the droplets of the aerosol mist do not have to pass through the flow channel 221 and thus do not encounter any surface which can trap the droplets. In another embodiment the substance supporting element 227 could be located at the Inlet end 223 of the flow channel 221. Such a configuration can be advantageous where the delivery predominantly of a vapour is required, as any droplets of an aerosol mist which are generated have to pass through the flow channel 221 and thus are likely to be trapped on a surface of the flow channel 221.

The substance supply unit 215 includes a frangible seal element 234 at the outlet end 225 of the flow channel 221, which seal element 234 acts normally to close the flow channel 221 and prevent the escape of substance therefrom, and, on operation of the gas supply unit 216, is opened to allow for the delivery of a gas flow through the flow channel 221. In this embodiment the seal element 234 is ruptured by the gas flow as generated by operation of the gas supply unit 216.

In this embodiment the gas supply unit 216 comprises a flexible bulb 236 which is squeezed by the user to deliver an air flow through the flow channel 221. In alternative embodiments other pump arrangements could be utilized.

Figure 22:
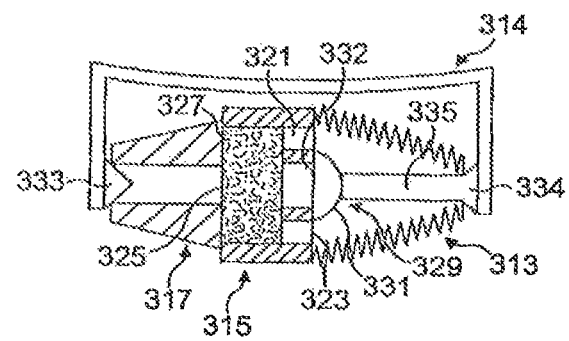
FIG. 22 illustrates a nasal delivery device in accordance with an eleventh embodiment of the present invention.
Figure 23:
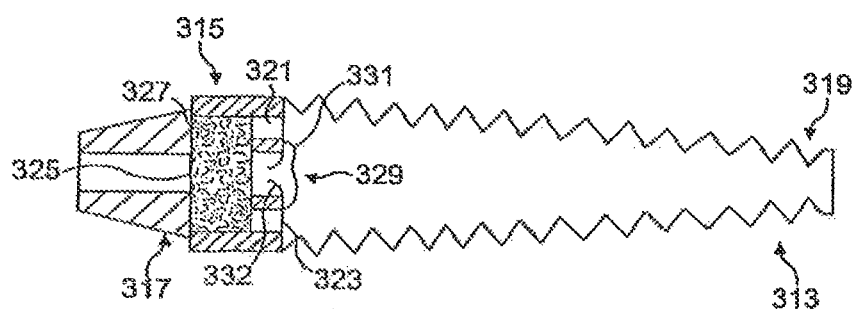
FIG. 23 illustrates the delivery device of FIG. 22 in the primed state.
Figure 24:
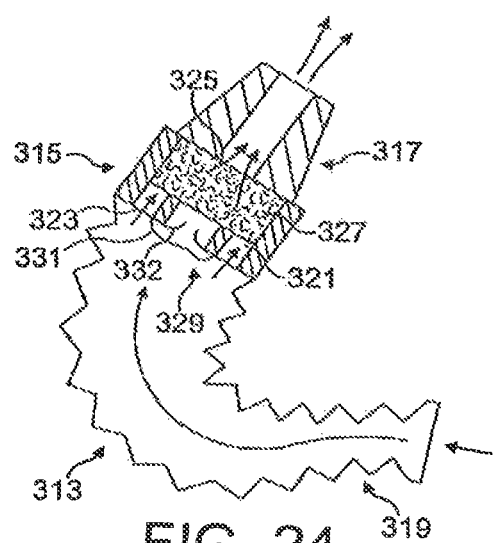
FIG. 24 illustrates the delivery device of FIG. 22 in the operative state.

FIGS. 22 to 24 illustrate a nasal delivery device in accordance with an eleventh embodiment of the present invention.

The delivery device comprises a delivery unit 313 for delivering substance, in this embodiment a decongestant, to be delivered as one or both of a vapor or a fine aerosol mist, and a sealing member 314 for sealing the delivery unit 313 in a closed, inoperative state.

The delivery unit 313 comprises a substance supply unit 315 for supplying substance to be delivered, a mouthpiece 317 through which a user exhales and which is fluidly connected to the substance supply unit 315 such as to cause substance to be entrained by the exhaled air flow, and a nosepiece 319 for fitting to a nostril of the user which is fluidly connected to the substance supply unit 315 such that the air flow entraining substance is delivered to the nasal airway of the user.

The substance supply unit 315 comprises a flow channel 321, one, inlet end 323 of which is fluidly connected to the mouthpiece 317 and the other, outlet end 325 of which is fluidly connected to the nosepiece 319, and a substance supporting element 327, in this embodiment a porous, absorbent element, which is disposed in the flow channel 321 and over which the entraining air flow is directed to entrain substance from the substance supporting element 327 where dosed with substance, as will be described in more detail hereinbelow.

The substance supply unit 315 further comprises a dosing unit 329 for dosing the substance supporting element 327 with a predetermined dose of substance. In this embodiment the dosing unit 329 comprises a flexible blister element 331 which contains the dose of substance, and a frangible closure element 332 which normally encloses the blister element 331 and is in fluid communication with the flow channel 321, such that depression of the blister element 331 acts to break the closure element 332 and causes the contained substance to be dosed onto the substance supporting element 327. In this embodiment the delivery device is configured such that the blister element 331 is depressed by squeezing, typically between the thumb and forefinger, the sealing member 314. In an alternative embodiment the delivery device could be configured by squeezing the delivery device, typically between the thumb and forefinger, such as to cause the mouthpiece 313 to act on the blister element 331.

In this embodiment the substance supporting element 327 and the formulation of the substance are such as to provide for sustained substance delivery over a period of time following dosing of the substance supporting element 327, thereby providing a device which can be used repeatedly, typically allowing for use over the period of a day.

In other embodiments, by control of the construction of the substance supporting element 327 and the formulation of the substance, the rate of release of the substance, and hence the rate of uptake of the substance in the entraining air flow, can be controlled. For example, the delivery device could be configured as a single-use, vapor delivery device, where the formulation would be volatile, allowing for the uptake of an entire dose of substance in a single use.

The mouthpiece 319 comprises a flexible, concertinaed body 320, in this embodiment formed of a plastics material, which is configured normally to adopt an expanded state when not restrained, as illustrated in FIG. 20, and in this embodiment is restrained by the sealing member 314 in a compressed state, as illustrated in FIG. 19. When in the expanded state, the body 320 can be bent such as to allow for insertion of the nosepiece 317 into a nostril of the user and the body 320 to be gripped in the mouth of the user.

The sealing member 314 comprises first and second sealing elements 333, 334 which are configured to seal the nosepiece 317 and the mouthpiece 319 of the delivery unit 313 in the collapsed, inoperative state, thereby preventing the Ingress of foreign material into the delivery unit 313 prior to use and the escape of substance from the delivery unit 313 subsequent to operation of the dosing unit 329, with the resilience of the body 320 of the mouthpiece 319 acting to maintain the sealing of the delivery unit 313. In this embodiment the second, mouthpiece sealing element 334 includes a projection 335 which extends into the mouthpiece 319 and provides for depression of the blister element 331 of the dosing unit 329 on squeezing the sealing member 314, typically between the thumb and forefinger.

In an alternative embodiment the dosing unit 329 could be disposed to the sealing member 314 such as to be located at the nosepiece 317, with the blister element 331 being depressed on squeezing the sealing member 314, typically between the thumb and forefinger, and the contained substance being dosed onto the substance supporting element 327.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 25:
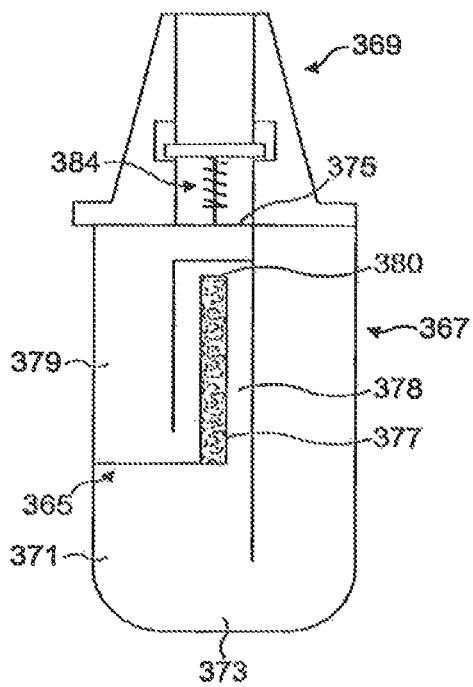
FIG. 25 illustrates a nasal delivery device in accordance with a twelfth embodiment of the present invention.
Figure 26:
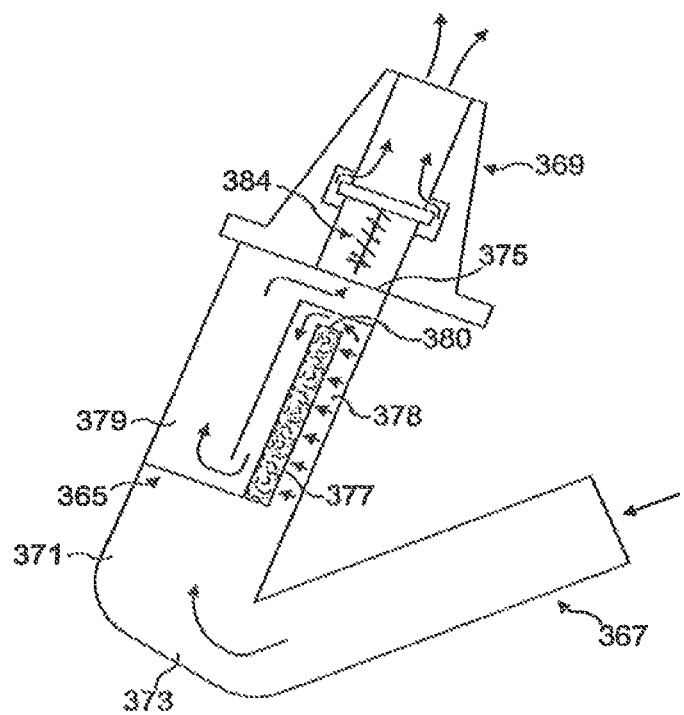
FIG. 26 illustrates the delivery device of FIG. 25 in the operative state.

FIGS. 25 and 26 illustrate a nasal delivery device in accordance with a twelfth embodiment of the present invention.

The delivery device comprises a substance supply unit 365 for supplying substance, in this embodiment a decongestant, to be delivered as one or both of a vapor or a fine aerosol mist, a mouthpiece 367 through which the user exhales and which is fluidly connected to the substance supply unit 365 such as to cause substance to be entrained by an exhaled air flow, and a nosepiece 369 for fitting to a nostril of the user which is fluidly connected to the substance supply unit 365 such that an air flow entraining substance is delivered to the nasal airway of the user.

The substance supply unit 365 comprises a flow channel 371, in this embodiment an elongate channel, one, inlet end 373 of which is fluidly connected to the mouthpiece 367 and the other, outlet end 375 of which is fluidly connected to the nosepiece 369, and a substance supporting element 377 which defines a part of the flow channel 371 and over a delivery surface of which the entraining air flow is directed to entrain substance from the substance supporting element 377 where dosed with substance, as will be described in more detail hereinbelow.

In this embodiment the flow channel 371 comprises a first, upstream flow channel section 378 which is fluidly connected to the mouthpiece 367 and into which an exhaled air flow is first delivered, a second, downstream flow channel section 379 which is fluidly connected to the nosepiece 369 and from which the exhaled air flow is delivered, and a flow resistor 380 which fluidly connects the upstream and downstream flow channel sections 378, 379. The flow resistor 380 is configured to provide a predetermined flow resistance to the delivered air flow and thereby maintain a predetermined pressure in the upstream flow channel section 378, the purpose of which will become apparent hereinbelow.

In this embodiment the substance supporting element 377 comprises a porous, capillary element which is loaded with substance and Is disposed such that a first, pressure surface thereof defines a part of the upstream flow channel section 378 and a second, delivery surface thereof, here a surface opposite the delivery surface, defines a part of the downstream flow channel section 379.

With this configuration, the developed pressure in the upstream flow channel section 378 acts to pressurize the pressure surface of the substance supporting element 377, which pressure in turn acts to drive substance through the capillaries and to the delivery surface of the substance supporting element 377, and the air flow which passes through the flow resistor 380 and the downstream flow channel section 379 acts to entrain substance presented at the delivery surface of the substance supporting element 377 in the downstream flow channel section 379.

With this configuration, the delivery device provides for repeated use until the substance supporting element 377 is exhausted of substance. Thus, by loading the substance supporting element 377 to differing degrees, the delivery device can be configured for use over different periods, for example, daily, weekly, etc.

It is envisaged that this configuration will find particular application in the delivery of a fine aerosol mist, where the substance presented from the capillaries at the delivery surface of the substance supporting element 377 is entrained as droplets, with the dimension of the droplets being determined by the dimension of the capillaries in the substance supporting element 377.

The substance supply unit 365 includes a one-way outlet valve 384 at the outlet end 375 of the flow channel 371, which valve 384 acts normally to close the flow channel 371 at the nosepiece 369 and prevent the escape of substance therefrom, and, on exhalation through the mouthpiece 367, is opened to allow for the delivery of an entraining air flow through the flow channel 371. In this embodiment, as will be described in more detail hereinbelow, the flow channel 371 is closed by the nosepiece 369 when returned to the closed position.

In this embodiment the mouthpiece 367 is hinged to the substance supply unit 365, here resiliently hinged as an integral unit, such as to be movable between a first, closed position in which the mouthpiece 367 is closed, here by the nosepiece 369, as illustrated in FIG. 25, and an open position in which the user can grip the same in his/her mouth, as illustrated in FIG. 26.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 27:
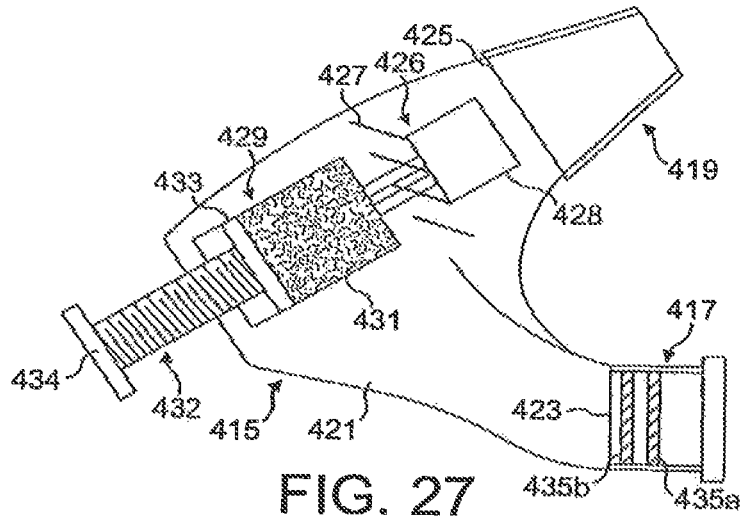
FIG. 27 illustrates a nasal delivery device in accordance with a thirteenth embodiment of the present invention.
Figure 28:
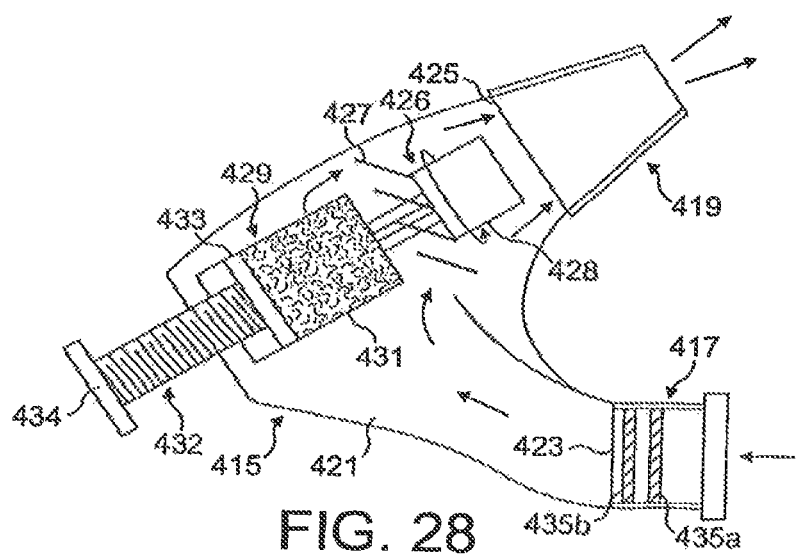
FIG. 28 illustrates the delivery device of FIG. 27 in the operative state.

FIGS. 27 and 28 illustrate a nasal delivery device in accordance with a thirteenth embodiment of the present invention.

The delivery device comprises a substance supply unit 415 for supplying substance, in this embodiment a decongestant, to be delivered as one or both of a vapor or a fine aerosol mist, a mouthpiece 417 through which the user exhales and which is fluidly connected to the substance supply unit 415 such as to cause substance to be entrained by an exhaled air flow, and a nosepiece 419 for fitting to a nostril of the user which is fluidly connected to the substance supply unit 415 such that an air flow entraining the substance is delivered to the nasal airway of the user.

The substance supply unit 415 comprises a flow channel 421, in this embodiment a chamber, one, inlet end 423 of which is fluidly connected to the mouthpiece 417 and the other, outlet end 425 of which is fluidly connected to the nosepiece 419, and a substance supporting unit 426 which is disposed in the flow channel 421 and over which the entraining air flow is directed to entrain substance from the substance supporting unit 426 where dosed with substance, as will be described in more detail hereinbelow.

The substance supporting unit 426 comprises a movable, in this embodiment rotatable member 427 which is rotated by the air flow driven though the flow channel 421, and a substance supporting element 428 which is disposed to the rotatable member 427 such as to be rotated by the same. In this embodiment the substance supporting element 428 comprises a capillary structure which is dosed with substance, and, on rotation of the substance supporting element 428, the substance is driven outwardly to a radially outward surface thereof, which substance presented at the capillaries is entrained by the entraining air flow.

The substance supply unit 415 further comprises a dosing unit 429 for dosing the substance supporting element 428 with a predetermined dose of substance, in this embodiment prior to each operation thereof.

In this embodiment the dosing unit 429 comprises a container 431 which contains a volume of substance and is operably fluidly connected to the substance supporting element 428, and a piston unit 432 which is operable to deliver a dose of substance from the container 431 to the substance supporting element 428.

In this embodiment the container 431 includes a one-way valve which acts to prevent ingress into the container 431.

In this embodiment the piston unit 432 comprises a piston 433 which is slideably disposed in sealing engagement with the container 431 and an actuating member 434 which is operable to drive the piston 432 to deliver a dose of substance from the container 431. In this embodiment the actuating member 434 comprises a rotatable member which is threadedly-engaged relative to the container 431 such as to be advanced into the container 431 on rotation of the same, which advancement of the actuating member 434 acts to drive the piston 433 into the container 431, with one complete revolution of the actuating member 434 being in this embodiment such as to deliver a metered dose of substance to the substance supporting element 428.

In an alternative embodiment the dosing unit 429 can comprise a squeeze bottle which provides for the delivery of a dose of substance on each actuation thereof, through squeezing the same. In a preferred embodiment the squeeze bottle is of a kind which includes a one-way outlet valve and a reservoir which reduces in volume on each actuation. With this configuration, air is not introduced into the reservoir, and advantageously a preservative-free liquid substance, either as a suspension or solution, can be utilized.

In this embodiment the delivery device is configured as a multi-use device which is dosed on each operation, allowing for the uptake of an entire dose of substance in a single use.

The delivery device further comprises at least one filter element 435, in this embodiment disposed in the mouthpiece 417, for filtering the exhaled air flow. In this embodiment the delivery device comprises a first, anti-microbial filter element 435a for filtering microbes from the exhaled air flow and a second, drying filter element 435b for de-humidifying the exhaled air flow and thereby promoting the uptake of substance through the flow channel 421.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 29:
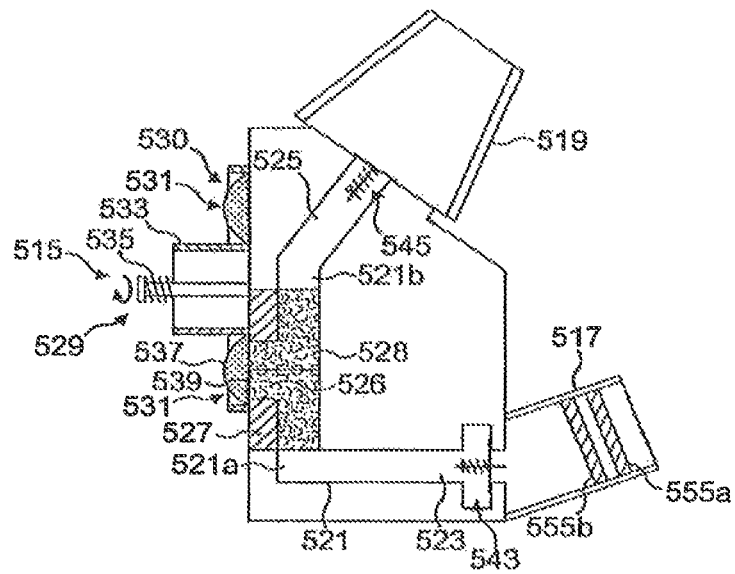
FIG. 29 illustrates a nasal delivery device in accordance with a fourteenth embodiment of the present invention.
Figure 30:
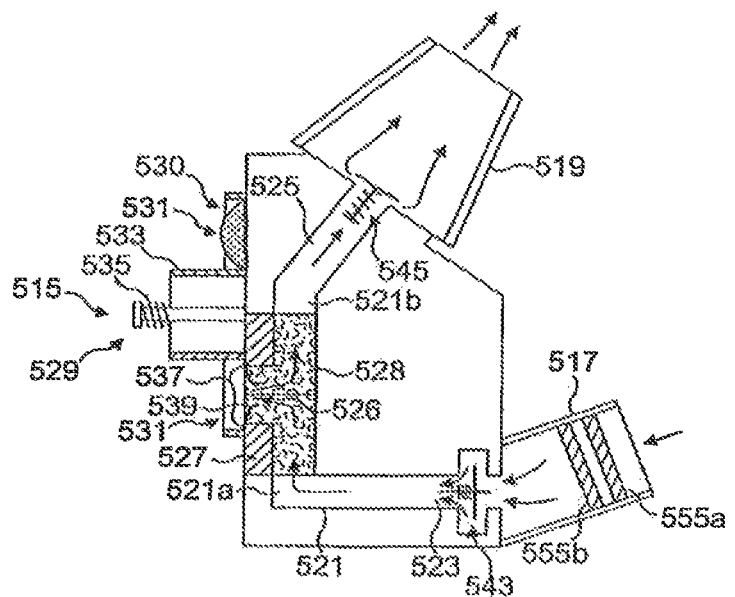
FIG. 30 illustrates the delivery device of FIG. 29 in the operative state.

FIGS. 29 and 30 illustrate a nasal delivery device in accordance with a fourteenth embodiment of the present invention.

The delivery device comprises a main body 514, a substance supply unit 515 which contains substance, in this embodiment a decongestant, to be delivered as one or both of a vapor or a fine aerosol mist, a mouthpiece 517 through which the user exhales and which is fluidly connected to the substance supply unit 515 such as to cause substance to be entrained by an exhaled air flow, and a nosepiece 519 for fitting to a nostril of the user which is fluidly connected to the substance supply unit 515 such that an air flow entraining the substance is delivered to the nasal airway of the user.

The substance supply unit 515 comprises a flow channel 521, one, inlet end 523 of which is fluidly connected to the mouthpiece 517 and the other, outlet end 525 of which is fluidly connected to the nosepiece 519.

The flow channel 521 includes a delivery port 526 at a location between, in this embodiment intermediate, the inlet and outlet ends 523, 525 thereof, and a sealing member 527, in this embodiment an annular member, which is disposed about the delivery port 526 and presents a sealing surface which sealing engages a blister pack member 530, as will be described in more detail hereinbelow.

In this embodiment the flow channel 521 comprises first and second channel parts 521a, 521b, the respective ends of which terminate at the delivery port 526, such that in use an air flow generated through the flow channel 521 is directed through the first channel part 521a into a blister element 531 of the blister pack member 530 which is located at the delivery port 526. In this way, the air flow acts to flush out any residual substance remaining in the blister element 531, thus ensuring the delivery of a complete dose of substance.

The substance supply unit 515 further comprises a substance supporting element 528, in this embodiment a porous, absorbent element, which is disposed in the flow channel 521 adjacent the delivery port 526, over which the entraining air flow is directed to entrain substance from the substance supporting element 528 where dosed with substance, as will be described in more detail hereinbelow.

The substance supply unit 515 further comprises a dosing unit 529 for dosing the substance supporting element 528 with a predetermined dose of substance.

In this embodiment the dosing unit 529 comprises a blister pack member 530 which includes a plurality of blister elements 531, which each contain a dose of substance, a support member 533 which is rotatably mounted to the main body 514 and supports the blister pack member 530, and a biasing element 535, in this embodiment a resilient element, here a compression spring, which acts to bias the support member 533, and hence the blister pack member 530 as supported thereby, against the main body 514, such as to maintain a selected one of the blister elements 531 in sealing engagement with the sealing member 527.

In this embodiment the blister elements 531 each comprise a flexible body member 537 and a frangible closure member 539 which normally encloses the body member 537. With this configuration, when a selected one of the blister elements 531 is located at the delivery port 526, the closure member 539 of the blister element 531 is in fluid communication with the flow channel 521, such that depression of the body member 537 of the blister element 531 acts to break the closure member 539 and causes the contained substance to be dosed onto the substance supporting element 528.

In this embodiment the formulation of the substance is such as to provide for delivery of the entire dose of substance in a single operation. For example, where the delivery device is configured as a vapor delivery device, the formulation would be volatile as to allow for the uptake of an entire dose of substance in a single use. In one embodiment the generated air flow can provide at least partially for vaporization of the substance.

The substance supply unit 515 includes a one-way inlet valve 543 at the Inlet end 523 of the flow channel 521 and a one-way outlet valve 545 at the outlet end 525 of the flow channel 521, which valves 543, 545 act normally to close the flow channel 521 and prevent the escape of substance therefrom, and, on exhalation through the mouthpiece 517, are opened to allow for the delivery of an entraining air flow through the flow channel 521.

The delivery device further comprises at least one filter element 555, in this embodiment disposed in the mouthpiece 517, for filtering the exhaled air flow. In this embodiment the delivery device comprises a first, anti-microbial filter element 555*a* for filtering microbes from the exhaled air flow and a second, drying filter element 555*b* for de-humidifying the exhaled air flow and thereby promoting the uptake of substance through the flow channel 521.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Figure 31:
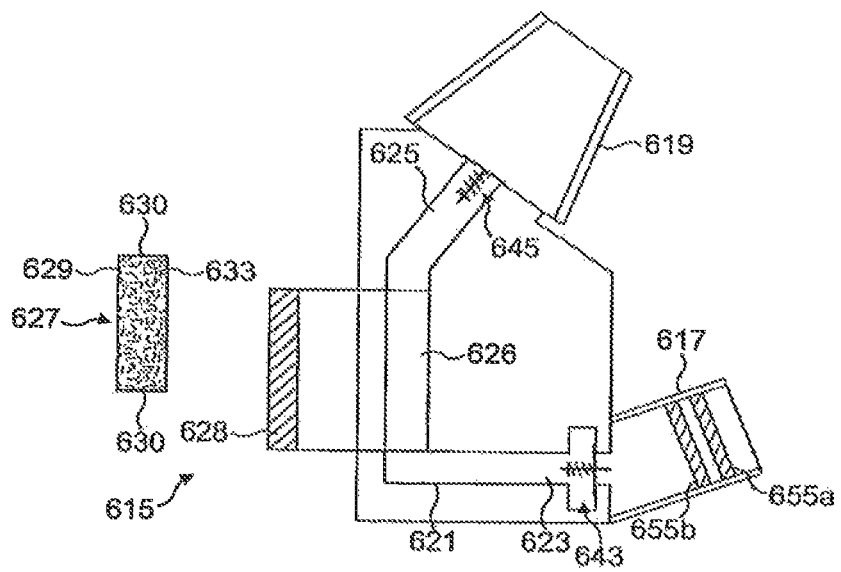
FIG. 31 illustrates a nasal delivery device in accordance with a fifteenth embodiment of the present invention.
Figure 32:
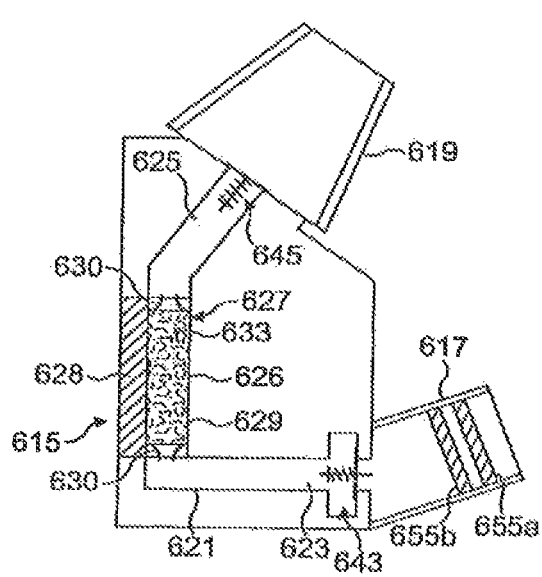
FIG. 32 illustrates the delivery device of FIG. 31 in the primed state.
Figure 33:
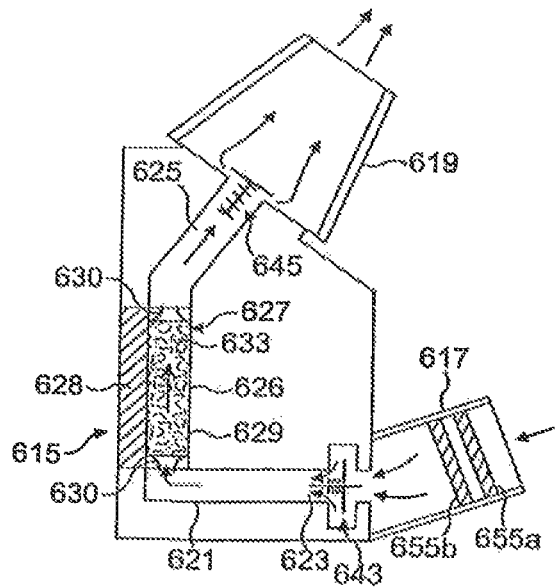
FIG. 33 illustrates the delivery device of FIG. 31 in the operative state.

FIGS. 31 to 33 illustrate a nasal delivery device in accordance with a fifteenth embodiment of the present invention.

The delivery device comprises a substance supply unit 615 which is operative to supply substance, in this embodiment a decongestant, to be delivered as one or both of a vapor or a fine aerosol mist, a mouthpiece 617 through which the user exhales and which is fluidly connected to the substance supply unit 615 such as to cause substance to be entrained by an exhaled air flow, and a nosepiece 619 for fitting to a nostril of the user which is fluidly connected to the substance supply unit 615 such that an air flow entraining the substance is delivered to the nasal airway of the user.

The substance supply unit 615 comprises a flow channel 621, one, inlet end 623 of which is fluidly connected to the mouthpiece 617 and the other, outlet end 625 of which is fluidly connected to the nosepiece 619, which includes a substance receiving chamber 626 which is configured to receive a substance dosing unit 627, as will be described in more detail hereinbelow. In this embodiment the flow channel 621 includes first and second flow channel sections 621*a*, 621*b*, which fluidly connect the respective ones of the mouthpiece 617 and the nosepiece 619 to the substance receiving chamber 626.

The substance supply unit 615 further comprises a dosing member 628 which is operable between an open position, as illustrated in FIG. 31, to allow for the insertion of a substance dosing unit 627 into the substance receiving chamber 626 and a closed position, as illustrated in FIGS. 32 and 33, in which the substance receiving chamber 626 is closed thereby.

In this embodiment the dosing member 628 includes a latch (not illustrated) which acts to latch the dosing member 628 in the closed position.

In this embodiment the substance dosing unit 627 is in the from of a cartridge which contains substance, in this embodiment a decongestant, to be delivered as one or both of a vapor or a fine aerosol mist.

In an alternative embodiment the delivery device could comprise a substance dosing assembly which includes a plurality of substance dosing units 627 and Is operable to present the substance dosing units 627 successively to the substance receiving chamber 626. In one embodiment the substance dosing assembly could include a belt which supports a plurality of substance dosing units 627, such as to allow the substance dosing units 627 to be drawn successively into the substance receiving chamber 626.

In this embodiment each substance dosing unit 627 comprises a flexible, elongate tubular body 629, frangible closure elements 630 at the respective ends of the tubular body 629 which normally enclose the same, and a porous, absorbent element 633 which is disposed in the tubular body 629, over which an entraining air flow is directed to entrain substance therefrom, as will be described in more detail hereinbelow.

In this embodiment the tubular body 629 is diametrally oversized relative to the diametric dimension of the substance receiving chamber 626, such that, on insertion of a substance dosing unit 627 into the substance receiving chamber 626 and with closure of the dosing member 628, the tubular body 629 is squeezed diametrally such as to rupture the closure elements 630, as illustrated in FIG. 32, and thereby open the substance dosing unit 627.

In this embodiment the formulation of the substance is such as to provide for delivery of the entire dose of substance in a single operation. For example, where the delivery device is configured as a vapor delivery device, the formulation would be sufficiently volatile as to allow for the uptake of an entire dose of substance in a single use. In one embodiment the generated air flow can provide at least partially for vaporization of the substance.

The substance supply unit 615 further comprises a one-way inlet valve 643 at the Inlet end of the flow channel 621 and a one-way outlet valve 645 at the outlet end of the flow channel 621, which valves 643, 645 act normally to close the flow channel 621 and prevent the escape of substance therefrom, and, on exhalation through the mouthpiece 617, are opened to allow for the delivery of an entraining air flow through the flow channel 621 and the substance receiving chamber 615.

The delivery device further comprises at least one filter element 655, in this embodiment disposed in the mouthpiece 617, for filtering the exhaled air flow. In this embodiment the delivery device comprises a first, anti-microbial filter element 655a for filtering microbes from the exhaled air flow and a second, drying filter element 655b for de-humidifying the exhaled air flow and thereby promoting the uptake of substance through the flow channel 621.

In this embodiment the delivery device is configured to deliver substance through one nostril of the user at such a pressure as to flow around the posterior margin of the nasal septum and out of the other nostril of the user, thereby achieving bi-directional delivery through the nasal cavities as disclosed in WO-A-00/51672, the content of which is herein incorporated by reference. In an alternative embodiment the delivery device could be configured to deliver substance at a reduced pressure which is not sufficient to achieve bi-directional delivery through the nasal cavities. Such an embodiment is still advantageous as compared to known delivery devices in providing for velum closure.

Finally, it will be understood that the present invention has been described in its preferred embodiments and can be modified in many different ways without departing from the scope of the Invention as defined in the appended claims.

For example, although the present invention has been embodied in relation to the use of decongestants, it will be understood that the present invention finds application in relation to all manner of substances, such as chemosensory substances.

In one modification, the delivery devices of the above-described embodiments which are configured to be used a predetermined number of times can include an indicator to indicate the state of the device. This indication can be quantitative by a representation of the number of available doses or qualitative, for example, through a colored indicator.

In another modification, the substance supply units 15, 65, 115, 165, 215, 265, 315, 365, 415, 515, 615 of the above-described embodiments could be configured to supply substance by vibration as achieved through the delivered air or gas flow.

In a further modification, the delivery devices can include caps on one or both of the mouthpieces and nosepieces. In these embodiments one or both of the Inlet and outlet valves could be omitted.

I claim:

1. A delivery device for delivering a substance to a nasal airway of a subject, comprising:
    a nosepiece having an inlet and an outlet for insertion into a first nostril of the subject;
    a substance supply unit for supplying the substance;
    a mouthpiece which is hinged to the substance supply unit and through which the subject in use exhales to deliver an entraining air flow, wherein the mouthpiece is movable between a first position, in which the mouthpiece is closed by at least a portion of the nosepiece, and a second position, in which the mouthpiece is opened and configured such that the subject can grip the mouthpiece in a mouth of the subject;
    and
    a flow channel that fluidly connects the mouthpiece to the nosepiece.

2. The device of claim 1, further comprising: a second nosepiece for insertion into a second nostril of the subject, and wherein the second nosepiece comprises a flow resistor.

3. The device of claim 1, wherein the entraining air flow is adapted to pass into one nasal passage of the subject and out of the other nasal passage of the subject, thereby achieving a bi-directional flow for delivering the substance to the nasal airway of the subject.

4. The device of claim 1, wherein the mouthpiece is resiliently hinged to the substance supply unit.

5. The device of claim 1, wherein the substance supply unit includes a valve which is selectively movable from a first position to close the flow channel and a second position to open the flow channel and allow for delivery of the entraining air flow through the flow channel.

* * * * *